United States Patent
Baker et al.

[11] Patent Number: 5,298,520
[45] Date of Patent: Mar. 29, 1994

[54] TRIAZOLE CONTAINING INDOLE DERIVATIVES

[75] Inventors: Raymond Baker, Much Hadham; Victor G. Matassa, Furneux Pelham; Leslie J. Street, Harlow, all of England

[73] Assignee: Merck Sharp & Dohme Limited, Hertfordshire, England

[21] Appl. No.: 827,187

[22] Filed: Jan. 28, 1993

[30] Foreign Application Priority Data

Feb. 1, 1991 [GB] United Kingdom ............... 9102222
Apr. 3, 1991 [GB] United Kingdom ............... 9106917
Jun. 21, 1991 [GB] United Kingdom ............... 9113415
Oct. 23, 1991 [GB] United Kingdom ............... 9122451

[51] Int. Cl.$^5$ .................... A61K 31/41; C07D 403/06
[52] U.S. Cl. .................... 514/383; 514/381; 514/397; 514/323; 546/201; 548/254; 548/312.1; 548/255; 548/266.4
[58] Field of Search ............ 548/266.4, 254, 255, 548/336; 546/201; 514/381, 383, 397, 323

[56] References Cited

U.S. PATENT DOCUMENTS

| | | | |
|---|---|---|---|
| 3,475,437 | 10/1969 | Landgraf et al. | 548/504 |
| 3,644,403 | 2/1972 | Rodriguez | 548/491 |
| 3,801,594 | 4/1974 | Poletto et al. | 548/504 |
| 4,138,570 | 2/1979 | Psaar | 548/491 |
| 4,453,001 | 6/1984 | Brand et al. | 548/466 |
| 4,618,617 | 10/1986 | Yamamato | 514/364 |
| 4,692,531 | 9/1987 | Algieri et al. | 548/193 |
| 4,839,377 | 9/1989 | Bays et al. | 514/415 |
| 4,851,406 | 7/1989 | Mertens et al. | 514/212 |
| 4,870,085 | 9/1989 | Glaser et al. | 514/323 |
| 5,037,845 | 8/1991 | Oxford | 514/415 |

FOREIGN PATENT DOCUMENTS 0200322 11/1986 European Pat. Off. .
0328200 8/1989 European Pat. Off. .
91/188897 12/1991 PCT Int'l Appl. .
2083463A 3/1982 European Pat. Off. .

OTHER PUBLICATIONS

Katritzky et al "Heterocyclic Chemistry" Oxford, 1964, pp. 232-233.
Journal of Medicinal Chemistry, vol. 30, No. 1, (Jan. 1987) Washington U.S. *R. A. Glenn, 'Central Serotonin Receptors as Targets for Drug Research'.
A. Doenicke, et al The Lancet, 1988, 1, 1309-11.
J. Neurosci. 7, 894, (1987) 1981.
Arch. Pharm., 342, 8 111 (1990) 1973.
J. Org. Chem., vol. 47, pp. 536-544 (1982) by Jose Elguero, et al., entitled *Synthesis and Physicochemical Properties of 1,2,b-Thiadiazine 1,1-Dioxides.*
Chem. Ber. vol. 111, pp. 1915-1971 (1978) by M. Preiss, entitled *1,2,5-Thiadiazolidin-1,1-dioxid und Homologe.*
Indian J. of Chem., vol. 21B, pp. 941-944 (Oct. 1982) by V. P. Arya,: et al., entitled *Nitroimidazoles; Part V-1-(-1-Methyl-5-nitroimidazol-2-yl)-1,2,4-triazolidin-3,5-diones & Analogues.*

Primary Examiner—Jane T. Fan
Assistant Examiner—C. Chang
Attorney, Agent, or Firm—Robert J. North

[57] ABSTRACT

A class of substituted imidazole, triazole and tetrazole derivatives are selective agonists of 5-HT$_1$-like receptors and are therefore useful in the treatment of clinical conditions, in particular migraine and associated disorders, for which a selective agonist of these receptors is indicated.

6 Claims, No Drawings

TRIAZOLE CONTAINING INDOLE DERIVATIVES

The present invention relates to a class of substituted imidazole, triazole and tetrazole derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309–11). The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and pediatric migraine.

EP-A-0313397 describes a class of tryptamine derivatives substituted by a five-membered heteroaliphatic ring, which are stated to be specific to a particular type of "5-HT$_1$-like" receptor and thus to be effective therapeutic agents for the treatment of clinical conditions, particularly migraine, requiring this activity. However, EP-A-0313397 neither discloses nor suggests the imidazole, triazole and tetrazole derivatives provided by the present invention.

The present invention provides a compound of formula I, or a salt or prodrug thereof:

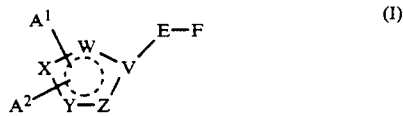

wherein the broken circle represents two non-adjacent double bonds in any position in the five-membered ring;

two, three or four of V, W, X, Y and Z represent nitrogen and the remainder represent carbon provided that, when two of V, W, X, Y and Z represent nitrogen and the remainder represent carbon, then the said nitrogen atoms are in non-adjacent positions within the five-membered ring;

A$^1$ represents hydrogen, hydrocarbon, a heterocyclic group, halogen, cyano, trifluoromethyl, —OR$^x$, —SR$^x$, —NR$^x$R$^y$, —NR$^x$COR$^y$, —NR$^x$CO$_2$R$^y$, —NR$^x$SO$_2$R$^y$, or —NR$^z$CTNR$^x$R$^y$;

A$^2$ represents a non-bonded electron pair when four of V, W, X, Y and Z represent nitrogen and the other represents carbon; or, when two or three of V, W, X, Y and Z represent nitrogen and the remainder represent carbon, A$^2$ represents hydrogen, hydrocarbon, a heterocyclic group, halogen, cyano, trifluoromethyl, —OR$^x$, —SR$^x$, —NR$^x$R$^y$, —NR$^x$COR$^y$, —NR$^x$CO$_2$R$^y$, —NR$^x$SO$_2$R$^y$, or —NR$^z$CTNR$^x$R$^y$;

E represents a bond or a straight or branched alkylene chain containing from 1 to 4 carbon atoms;

F represents a group of formula

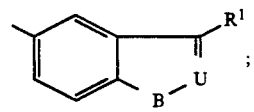

U represents nitrogen or C—R$^2$;
B represents oxygen, sulphur or N—R$^3$;
R$^1$ represents —CH$_2$.CHR$^4$.NR$^6$R$^7$ or a group of formula

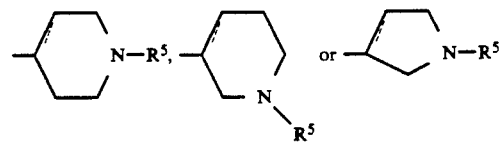

in which the broken line represents an optional chemical bond;

R$^2$, R$^3$, R$^4$, R$^5$, R$^6$ and R$^7$ independently represent hydrogen or C$_{1-6}$ alkyl;

R$^x$ and R$^y$ independently represent hydrogen, hydrocarbon or a heterocyclic group, or R$^x$ and R$^y$ together represent a C$_{2-6}$ alkylene group;

R$^z$ represents hydrogen, hydrocarbon or a heterocyclic group;

T represents oxygen, sulphur or a group of formula =N.G; and

G represents hydrocarbon, a heterocyclic group or an electron-withdrawing group.

The present invention also provides compounds of formula I above wherein three or four of V, W, X, Y and Z represent nitrogen and the remainder represent carbon;

A$^2$ represents a non-bonded electron pair when four of V, W, X, Y and Z represent nitrogen and the other represents carbon; or, when three of V, W, X, Y and Z represent nitrogen and the remainder represent carbon, A$^2$ represents hydrogen, hydorcarbon, a heterocyclic group, halogen, cyano, trifluoromethyl, —OR$^x$, —SR$^x$, —NR$^x$R$^y$, —NR$^x$COR$^y$, —NR$^x$CO$_2$R$^y$, —NR$^x$SO$_2$R$^y$, or —NR$^z$CTNR$^x$R$^y$; and A$^1$, E, F, R$^x$, R$^y$ R$^z$ and T are as defined above.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

A particular aryl group is phenyl.

Particular aryl($C_{1-6}$)alkyl groups include benzyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl ($C_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl ($C_{1-6}$) alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl ($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When the group G represents an electronwithdrawing group, this group is suitably cyano, nitro, $-COR^x$, $-CO_2R^x$ or $-SO_2R^x$, in which $R^x$ is as defined above.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

It will be appreciated that the imidazole, triazole and tetrazole rings of formula I can exist in a variety of canonical forms. These may suitably be represented by formulae IA to IT as follows:

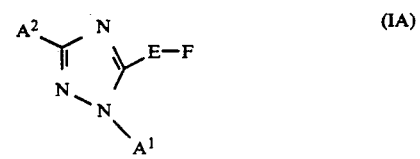
(IA)

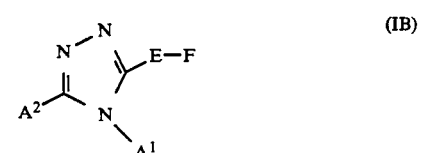
(IB)

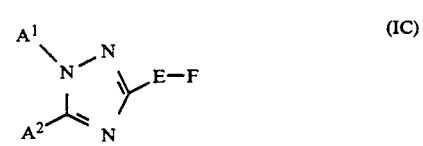
(IC)

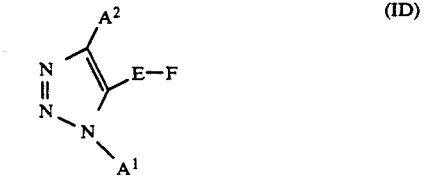
(ID)

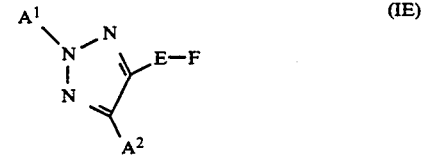
(IE)

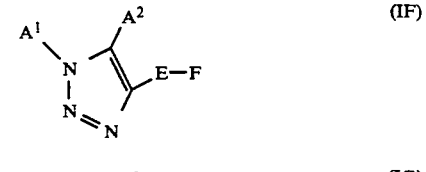
(IF)

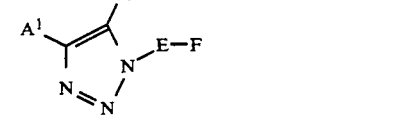
(IG)

-continued

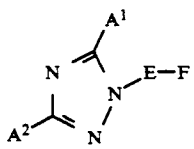
(IH)

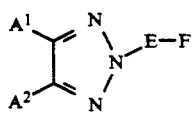
(IJ)

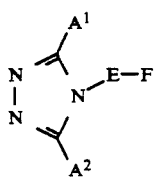
(IK)

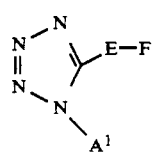
(IL)

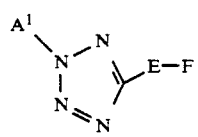
(IM)

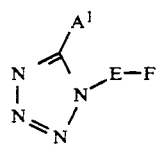
(IN)

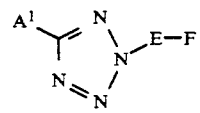
(IP)

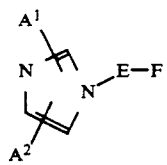
(IQ)

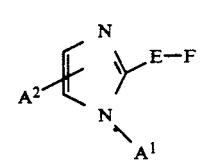
(IR)

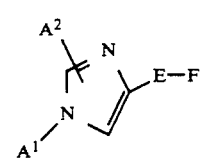
(IS)

-continued

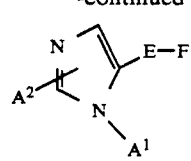
(IT)

wherein $A^1$, $A^2$, E and F are as defined above. Preferred imidazole, triazole and tetrazole rings of formula I include the rings represented by formulae IA, IC, IG, IH, IL, IM, IN, IP and IQ above, especially IH.

The alkylene chain E may be, for example, methylene, ethylene, 1-methylethylene, propylene or 2-methylpropylene. Alternatively, the group E may represent a single bond such that the group F in formula I is attached directly to the five-membered heteroaromatic ring.

The group F is suitably an indole, benzofuran or benzthiophene moiety of formula FA, or an indazole moiety of formula FB:

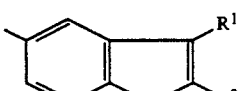
(FA)

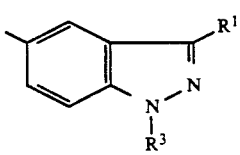
(FB)

wherein B, $R^1$, $R^2$ and $R^3$ are as defined above. Preferably, the group F represents an indole moiety of structure FC:

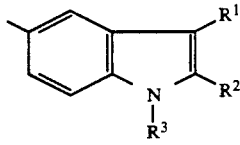
(FC)

wherein $R^1$, $R^2$ and $R^3$ are as defined above, in particular wherein $R^2$ and $R^3$ are both hydrogen.

It will be appreciated that when four of V, W, X, Y and Z represent nitrogen and the other represents carbon, i.e. when the ring of formula I is a tetrazole ring, then the group $A^2$ will be a non-bonded electron pair. Otherwise, $A^1$ and $A^2$ will independently represent hydrogen, hydrocarbon, a heterocyclic group, halogen, cyano, trifluoromethyl, —$OR^x$, —$SR^x$, —$NR^xR^y$, —$NR^xCOR^y$, —$NR^xCO_2R^y$, —$NR^xSO_2R^y$, or —$NR^zCTNR^xR^y$.

Suitable values for the groups $A^1$ and/or $A^2$ include $C_{1-6}$ alkyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted; and hydrogen, halogen, cyano, trifluoromethyl, $C_{1-6}$ alkoxy, $C_{1-6}$ alkylthio or —$NR^xR^y$, in which $R^x$ and $R^y$ are as defined above. Examples of optional substituents on the groups $A^1$ and/or $A^2$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^1$ and/or $A^2$ include hydrogen, methyl, methoxymethyl, aminomethyl, dimethylaminomethyl, acetylaminomethyl, benzoylaminomethyl, t-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, benzyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, pyridylmethyl, methoxypyridylmethyl, amino, methylamino, benzylamino, dimethylamino, t-butoxycarbonylaminoethylamino and methylsulphonylaminoethylamino.

Preferred values of $A^1$ and/or $A^2$ include hydrogen, methyl, ethyl, benzyl and amino.

Representative values of $R^1$ include aminoethyl, N-methylaminoethyl, N,N-dimethylaminoethyl, 4-piperidyl, 1-methyl-4-piperidyl, 3-pyrrolidinyl and 1-methyl-3-pyrrolidinyl.

Preferred values for the groups $R^2$ to $R^7$ are hydrogen and methyl.

A particular sub-class of compounds according to the invention is represented by the compounds of formula IIA, and salts and prodrugs thereof:

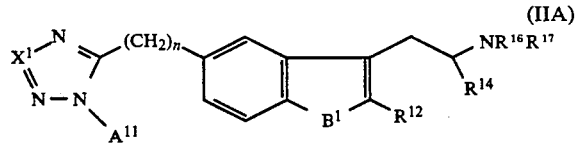

wherein $X^1$ represents nitrogen or $A^{12}$—C;

n is zero, 1, 2 or 3;

$B^1$ represents oxygen, sulphur or N—$R^{13}$;

$A^{11}$ and $A^{12}$ independently represent $C_{1-6}$ alkyl, $C_{2-6}$ alkenyl, $C_{2-6}$ alkynyl, $C_{3-7}$ cycloalkyl, aryl, aryl ($C_{1-6}$)alkyl, $C_{3-7}$ heterocycloalkyl, heteroaryl or heteroaryl ($C_{1-6}$)alkyl, any of which groups may be optionally substituted; or hydrogen, halogen, cyano, trifluoromethyl, $C_{1-6}$ alkoxy, $C_{1-6}$ alkylthio or —$NR^xR^y$;

$R^{12}$, $R^{13}$, $R^{14}$, $R^{16}$ and $R^{17}$ independently represent hydrogen or $C_{1-6}$ alkyl; and $R^x$ and $R^y$ independently represent hydrogen, hydrocarbon or a heterocyclic group, or $R^x$ and $R^y$ together represent a $C_{2-6}$ alkylene group.

Examples of optional substituents on the groups $A^{11}$ and $A^{12}$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^{11}$ and $A^{12}$ with respect to formula IIA include hydrogen, methyl, ethyl, benzyl and amino. When $X^1$ represents $A^{12}$—C, the group $A^{11}$ is preferably hydrogen or methyl.

Preferably, $R^{12}$, $R^{13}$ and $R^{14}$ each represents hydrogen. Preferred values of $R^{16}$ and $R^{17}$ with respect to formula IIA include hydrogen and methyl.

Another sub-class of compounds according to the invention is represented by the compounds of formula IIB, and salts and prodrugs thereof:

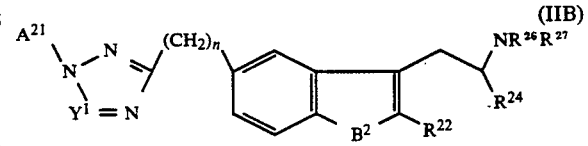

wherein $Y^1$ represents nitrogen or $A^{22}$—C;

n is zero, 1, 2 or 3;

$B^2$ represents oxygen, sulphur or N—$R^{23}$;

$A^{21}$ and $A^{22}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted; or hydrogen, halogen, cyano, trifluoromethyl, $C_{1-6}$ alkoxy, $C_{1-6}$ alkylthio or —$NR^xR^y$;

$R^{22}$, $R^{23}$, $R^{24}$, $R^{26}$ and $R^{27}$ independently represent hydrogen or $C_{1-6}$ alkyl; and $R^x$ and $R^y$ independently represent hydrogen, hydrocarbon or a heterocyclic group, or $R^x$ and $R^y$ together represent a $C_{2-6}$ alkylene group.

Examples of optional substituents on the groups $A^{21}$ and $A^{22}$ correspond to those indicated for the groups $A^{11}$ and $A^{12}$ with respect to formula IIA above. Particular values of $A^{21}$ and $A^{22}$ with respect to formula IIB include hydrogen, methyl, ethyl and benzyl.

Preferably, $R^{22}$, $R^{23}$ and $R^{24}$ each represents hydrogen. Preferred values of $R^{26}$ and $R^{27}$ with respect to formula IIB include hydrogen and methyl.

A further sub-class of compounds according to the invention is represented by the compounds of formula IIC, and salts and prodrugs thereof:

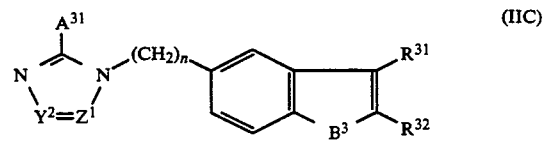

wherein $Y^2$ represents nitrogen or $A^{32}$—C;

$Z^1$ represents nitrogen or CH;

n is zero, 1, 2 or 3;

$B^3$ represents oxygen, sulphur or $N-R^{33}$;

$A^{31}$ and $A^{32}$ independently represent $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted; or hydrogen, halogen, cyano, trifluoromethyl, $C_{1-6}$ alkoxy, $C_{1-6}$ alkylthio or $-NR^xR^y$;

$R^{31}$ represents $-CH_2.CHR^{34}.NR^{36}R^{37}$ or a group of formula

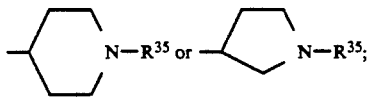

$R^{32}$, $R^{33}$, $R^{34}$, $R^{35}$, $R^{36}$ and $R^{37}$ independently represent hydrogen or $C_{1-6}$ alkyl; and $R^x$ and $R^y$ independently represent hydrogen, hydrocarbon or a heterocyclic group, or $R^x$ and $R^y$ together represent a $C_{2-6}$ alkylene group.

Examples of optional substituents on the groups $A^{31}$ and $A^{32}$ correspond to those indicated for the groups $A^{11}$ and $A^{12}$ with respect to formula IIA above. Particular values of $A^{31}$ and $A^{32}$ with respect to formula IIC include hydrogen, methyl and amino.

Preferably, $R^{32}$, $R^{33}$ and $R^{34}$ each represents hydrogen. Preferred values of $R^{35}$, $R^{36}$ and $R^{37}$ include hydrogen and methyl.

A still further sub-class of compounds according to the invention is represented by the compounds of formula IID, and salts and prodrugs thereof;

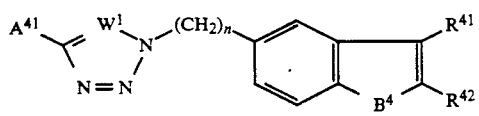

wherein $W^1$ represents nitrogen or $C-A^{42}$;

n is zero, 1, 2 or 3;

$B^4$ represents oxygen, sulphur or $N-R^{43}$;

$A^{41}$ and $A^{42}$ independently represent $C_{1-6}$ alkyl, $C_{2-6}$ alkenyl, $C_{2-6}$ alkynyl, $C_{3-7}$ cycloalkyl, aryl, aryl ($C_{1-6}$)alkyl, $C_{3-7}$ heterocycloalkyl, heteroaryl or heteroaryl ($C_{1-6}$)alkyl, any of which groups may be optionally substituted; or hydrogen, halogen, cyano, trifluoromethyl, $C_{1-6}$ alkoxy, $C_{1-6}$ alkylthio or $-NR^xR^y$;

$R^{41}$ represents $-CH_2.CHR^{44}.NR^{46}R^{47}$ or a group of formula

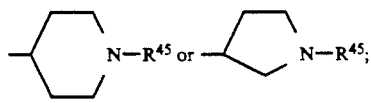

$R^{42}$, $R^{43}$, $R^{44}$, $R^{45}$, $R^{46}$ and $R^{47}$ independently represent hydrogen or $C_{1-6}$ alkyl; and $R^x$ and $R^y$ independently represent hydrogen, hydrocarbon or a heterocyclic group, or $R^x$ and $R^y$ together represent a $C_{2-6}$ alkylene group.

Examples of optional substituents on the groups $A^{41}$ and $A^{42}$ correspond to those indicated for the groups $A^{11}$ and $A^{12}$ with respect to formula IIA above. Particular values of $A^{41}$ and $A^{42}$ with respect to formula IID include hydrogen and methyl.

Preferably, $R^{42}$, $R^{43}$ and $R^{44}$ each represents hydrogen. Preferred values of $R^{45}$, $R^{46}$ and $R^{47}$ include hydrogen and methyl.

Specific compounds within the scope of the present invention include:

2-[5-(2-benzyltetrazol-5-ylmethyl)-1H-indol-3-yl]ethylamine;

2-[5-(1-benzyltetrazol-5-ylmethyl)-1H-indol-3-yl]ethylamine;

N,N-dimethyl-2-[5-(1-methyltetrazol-5-ylmethyl)-1H-indol-3-yl]ethylamine;

N,N-dimethyl-2-[5-(2-methyltetrazol-5-ylmethyl)-1H-indol-3-yl]ethylamine;

N,N-dimethyl-2-[5-(1,2,4-triazol-1-ylmethyl)-1H-indol-3-yl]ethylamine;

N,N-dimethyl-2-[5-(tetrazol-2-ylmethyl)-1H-indol-3-yl]ethylamine;

N,N-dimethyl-2-[5-(tetrazol-1-ylmethyl)-1H-indol-3-yl]ethylamine;

N,N-dimethyl-2-[5-(1-methyl-1,2,4-triazol-5-ylmethyl)-1H-indol-3-yl]ethylamine;

N,N-dimethyl-2-[5-(1-methyl-1,2,4-triazol-3-ylmethyl)-1H-indol-3-yl]ethylamine;

N,N-dimethyl-2-[5-(1,2,3-triazol-1-ylmethyl)-1H-indol-3-yl]ethylamine;

3-(2-aminoethyl)-5-(1-methyltetrazol-5-yl)-benzo[b]thiophene;

3-(2-aminoethyl)-5-(2-methyltetrazol-5-yl)-benzo[b]thiophene;

3-[2-(N,N-dimethylamino)ethyl]-5-(2-methyltetrazol-5-yl)benzo[b]thiophene;

N,N-dimethyl-2-[5-(2-methylimidazol-1-ylmethyl)-1H-indol-3-yl]ethylamine;

N,N-dimethyl-2-[5-(imidazol-1-ylmethyl)-1H-indol-3-yl]ethylamine;

N,N-dimethyl-2-[5-(2-methylimidazol-1-yl)-1H-indol-3-yl]ethylamine;

N,N-dimethyl-2-[5-(2-ethyltetrazol-5-ylmethyl)-1H-indol-3-yl]ethylamine;

N,N-dimethyl-2-[5-(1-ethyltetrazol-5-ylmethyl)-1H-indol-3-yl]ethylamine;

N,N-dimethyl-2-[5-(1,2,4-triazol-1-yl)-1H-indol-3-yl]ethylamine;

1-methyl-4-[5-(2-methylimidazol-1-yl)-1H-indol-3-yl]piperidine;

1-methyl-4-[5-(1,2,4-triazol-1-ylmethyl)-1H-indol-3-yl]piperidine;

4-[5-(2-methylimidazol-1-yl)-1H-indol-3-yl]piperidine;

4-[5-(1,2,4-triazol-1-ylmethyl)-1H-indol-3-yl]piperidine;

3-[5-(2-methylimidazol-1-yl)-1H-indol-3-yl]pyrrolidine;

1-methyl-3-[5-(2-methylimidazol-1-yl)-1H-indol-3-yl]pyrrolidine;

4-[5-(imidazol-1-yl)-1H-indol-3-yl]piperidine;

4-[5-(1,2,3-triazol-1-yl)-1H-indol-3-yl]piperidine;

1-methyl-4-[5-(imidazol-1-yl)-1H-indol-3-yl]piperidine;

1-methyl-4-[5-(1,2,3-triazol-1-yl)-1H-indol-3-yl]piperidine;

1-methyl-3-[5-(1,2,3-triazol-1-yl)-1H-indol-3-yl]pyrrolidine;

1-methyl-3-[5-(2-methylimidazol-1-ylmethyl)-1H-indol-3-yl]pyrrolidine;

1-methyl-3-[5-(imidazol-1-yl)-1H-indol-3-yl]pyrrolidine;

1-methyl-3-[5-(1,2,4-triazol-1-ylmethyl)-1H-indol-3-yl]pyrrolidine;

1-methyl-3-[5-(imidazol-1-ylmethyl)-1H-indol-3-yl]pyrrolidine;

N,N-dimethyl-2-[5-(2-aminoimidazol-1-yl)-1H-indol-3-yl]ethylamine;
N,N-dimethyl-2-[5-(2-aminoimidazol-1-ylmethyl)-1H-indol-3-yl]ethylamine;
N-methyl-2-[5-(1,2,4-triazol-1-ylmethyl)1H-indol-3-yl]ethylamine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The 1,2,4-triazole compounds of this invention may be prepared by a process which comprises reacting a reactive derivative of a carboxylic acid of formula $R^a$—$CO_2H$ with a compound either of formula III or of formula IV, or a salt thereof:

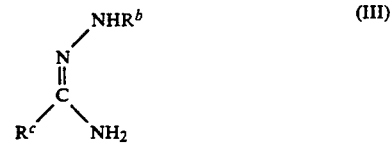

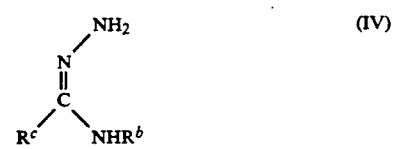

wherein one of $R^a$, $R^b$ and $R^c$ is a group of formula $A^1$, another is a group of formula $A^2$, and the third is a group of formula —E—F, as defined with reference to formula I above.

Suitable reactive derivatives of the acid $R^a$—$CO_2H$ include esters, for example $C_{1-4}$ alkyl esters; thioesters, for example pyridylthioesters; acid anhydrides, for example $(R^a$—$CO)_2O$; acid halides, for example acid chlorides; orthoesters; and primary, secondary and tertiary amides.

A preferred reactive derivative of the acid $R^a$—$CO_2H$ is the iminoether derivative of formula V:

where R is $C_{1-4}$ alkyl.

The reagent of formula III may be generated in situ in the reactive mixture. For example, the reaction may be effected by treating a compound of formula V above with an alkyl hydrazine, e.g. methyl hydrazine, followed by a suitable carboxylic acid such as formic acid.

The reaction is conveniently carried out by heating the reagents together, optionally in a solvent, for example tetrahydrofuran, dimethylformamide or a lower alkanol such as ethanol, propanol or isopropanol, at about 20° C. to 100° C. for about 1 to 6 hours.

Where $R^a$ is a group of formula —E—F and the group F is an indole moiety of structure FC as defined above, the reactive derivative of a carboxylic acid of formula $HO_2C$—E—F may be prepared by reacting a compound of formula VI:

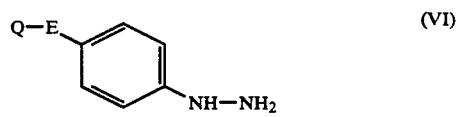

wherein Q represents a reactive carboxylate moiety, and E is as defined above; with a compound of formula VII or a carbonyl-protected form thereof:

wherein $R^2$ is as defined above and $R^{11}$ corresponds to the group $R^1$ as defined above or represents a group of formula —$CH_2.CHR^4D^1$, in which $R^4$ is as defined above and $D^1$ represents a readily displaceable group; followed, where required, by N-alkylation by standard methods to introduce the moiety $R^3$.

Suitable carbonyl-protected forms of the compounds of formula VII include the dimethyl acetal or ketal derivatives.

The readily displaceable group $D^1$ in the compounds of formula VII suitably represents a halogen atom, preferably chlorine. When the moiety $R^{11}$ in the compounds of formula VII is a group of formula $-CH_2.CHR^4D^1$, the substituent $D^1$ is displaced in situ under the prevailing reaction conditions to afford a final product of formula I wherein $R^1$ represents a group of formula $-CH_2.CHR^4.NH^2$. The terminal amino group can subsequently, if desired, be further elaborated using techniques known from the art to give a compound of formula I wherein $R^1$ represents the required group of formula $-CH_2.CHR^4.NR^6R^7$.

The reaction of compounds VI and VII may be carried out in a single step (Fischer indole synthesis) or by an initial non-cyclising step at a lower temperature to give a compound of formula VIII:

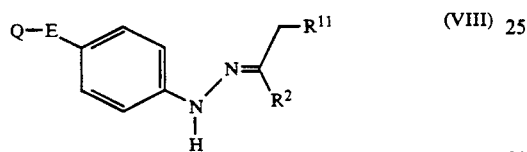

wherein Q, E, $R^2$ and $R^{11}$ are as defined above; followed by cyclisation using a suitable reagent, such as a polyphosphate ester, to give a compound of formula Q—E—F.

The hydrazines of formula VI may be prepared from the corresponding anilines of formula IX:

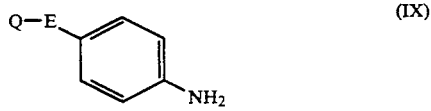

wherein Q and E are as defined above; by diazotisation followed by reduction. Diazotisation is typically carried out using sodium nitrite/conc. HCl and the resulting diazo product reduced in situ using, for example, tin(II) chloride/conc. HCl or sodium sulphite/conc. HCl.

The anilines of formula IX may be prepared by reduction of the corresponding nitro compounds of formula X:

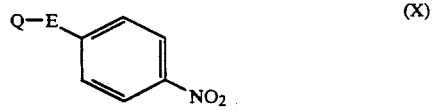

wherein Q and E are as defined above; typically by catalytic hydrogenation or using tin(II) chloride.

Where they are not commercially available, the nitro compounds of formula X may be synthesized by standard methods well known to those skilled in the art.

Where $R^a$ is a group of formula —E—F and the group F is an indazole moiety of structure FB as defined above, the reactive derivative of a carboxylic acid of formula $HO_2C$—E—F may be prepared by the cyclisation of a compound of formula XI:

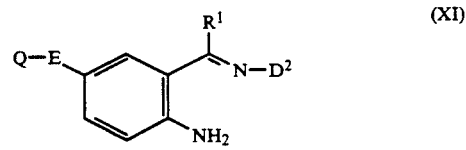

wherein Q, E and $R^1$ are as defined above; and $D^2$ represents a readily displaceable group; followed, where required, by N-alkylation by standard methods to introduce the moiety $R^3$.

The cyclisation of compound XI is conveniently achieved in a suitable organic solvent at an elevated temperature, for example in a mixture of m-xylene and 2,6-lutidine at a temperature in the region of 140° C.

The readily displaceable group $D^2$ in the compounds of formula XI suitably represents a $C_{1-4}$ alkanoyloxy group, preferably acetoxy. Where $D^2$ in the desired compound of formula XI represents acetoxy, this compound may be conveniently prepared by treating a carbonyl compound of formula XII:

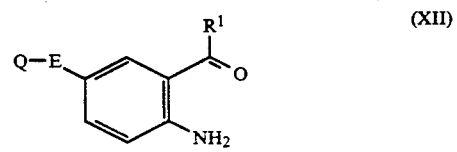

wherein $R^1$, E and Q are as defined above; or a protected derivative thereof; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivative of the intermediate of formula XII may be conveniently prepared by ozonolysis of an indole derivative of formula XIII:

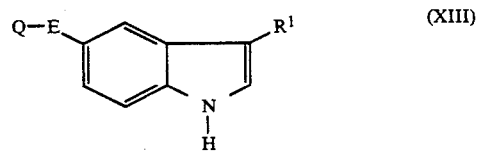

wherein $R^1$, E and Q are as defined above; followed by a reductive work-up, advantageously using dimethylsulphide.

The indole derivative of formula XIII may be prepared by methods analogous to those described in the accompanying Examples, or by procedures well known from the art.

In an alternative process, the triazole compounds according to the invention may be prepared by a method which comprises reacting a compound of formula XIV:

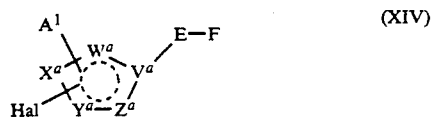

wherein $A^1$, E and F are as defined above, Hal represents halogen, and two of $V^a$, $W^a$, $X^a$, $Y^a$ and $Z^a$, to one of which the group Hal is attached, represent carbon and the remainder represent nitrogen; with a reagent which provides an anion $^-A^2$, where $A^2$ is as previously defined.

Reagents which may provide the anion $^-A^2$ include Grignard reagents $A^2MgHal$ (where Hal=halogen); organocuprate reagents such as $LiA^2{}_2Cu$; organolithium reagents $A^2Li$; or compounds which stabilise the anion by means of an adjacent activating group such as an ester or enolisable ketone function. In this case, the adjacent ester or ketone function may be retained after the process is complete, or may be removed. For example, an ester moiety may be hydrolysed and decarboxylated.

The 1,2,3-triazole compounds according to the present invention may be prepared by a process which comprises the cycloaddition of an alkyne of formula $R^a$—C≡C—$R^b$ with an azide of formula $R^c$—$N_3$, where $R^a$, $R^b$ and $R^c$ are as defined above.

The cycloaddition reaction may be conveniently effected in a suitable solvent such as tetrahydrofuran, ideally by heating in an autoclave for 8 hours.

The tetrazole compounds in accordance with the invention may be prepared by a process which comprises the cycloaddition of a nitrile of formula N≡C—$R^d$ with an azide of formula $R^e$—$N_3$, where one of $R^d$ and $R^e$ represents a group of formula $A^1$ and the other is a group of formula —E—F, as defined previously.

The cycloaddition reaction is conveniently effected by heating the reactants together at an elevated temperature, e.g. a temperature in the region of 150° C., in a suitable solvent such as N-methylpyrrolid-2-one, advantageously in the presence of triethylamine hydrochloride. The product obtained from the cycloaddition reaction will generally be a mixture of isomers substituted by the $A^1$ group at positions 1 and 2 of the tetrazole ring, corresponding to structures IL and IM respectively as defined above. These isomers may conveniently be separated using conventional techniques such as chromatography.

In an alternative process, the tetrazole compounds of the invention may be prepared by a method which comprises reacting a compound of formula $R^e$-L with a tetrazole derivative of formula XV:

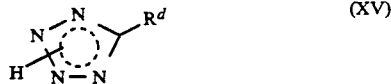
(XV)

wherein one of $R^d$ and $R^e$ represents a group of formula $A^1$ and the other is a group of formula —E—F, as defined above, and L represents a suitable leaving group; in the presence of a base such as triethylamine.

The leaving group L suitably represents halogen, e.g. bromine or iodine, or a sulphonate derivative such as tosylate or mesylate.

The reaction is conveniently carried out in a suitable organic solvent, e.g. acetonitrile, at room temperature.

The tetrazole derivatives of formula XV may be prepared by cycloaddition of a nitrile of formula N≡C—$R^d$ with sodium azide, advantageously under the conditions described above for the reaction between the nitrile N≡C—$R^d$ and the azide $R^e$—$N_3$; followed by acidification with a mineral acid such as hydrochloric acid.

In a further process, the compounds according to the invention wherein the group F is an indole moiety of structure FC as defined above may be prepared by a method which comprises reacting a compound of formula XVI:

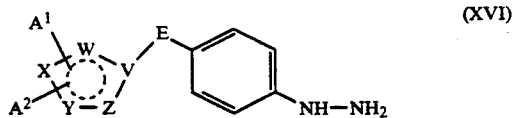
(XVI)

wherein V, W, X, Y, Z, $A^1$, $A^2$ and E are as defined above; with a compound of formula VII as defined above, or a carbonyl-protected form thereof, e.g. the dimethyl acetal or ketal; followed, where required, by N-alkylation by standard methods to introduce the moiety $R^3$.

As with that between compounds VI and VII, the reaction between compounds XVI and VII may be carried out in a single step (Fischer indole synthesis) or by an initial non-cyclising step at a lower temperature to give a compound of formula XVII:

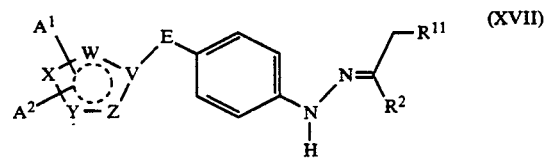
(XVII)

wherein V, W, X, Y, Z, $A^1$, $A^2$, E, $R^2$ and $R^{11}$ are as defined above; followed by cyclisation using a suitable reagent, e.g. a polyphosphate ester.

The hydrazines of formula XVI may be prepared from the corresponding anilines of formula XVIII:

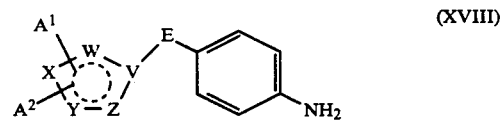
(XVIII)

wherein V, W, X, Y, Z, $A^1$, $A^2$ and E are as defined above; by methods analogous to those described above with reference to the compounds of formula IX.

The anilines of formula XVIII may be prepared from the corresponding nitro compounds of formula XIX:

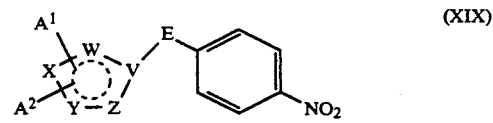
(XIX)

wherein V, W, X, Y, Z, $A^1$, $A^2$ and E are as defined above; by methods analogous to those described above with reference to the compounds of formula X.

The nitro compounds of formula XIX may be prepared by a variety of methods which will be readily apparent to those skilled in the art. For example, where V represents a nitrogen atom, the relevant compounds of formula XIX may be prepared by reacting the anion of a compound of formula XX with a compound of formula XXI:

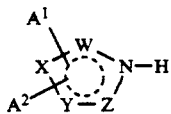

(XX)

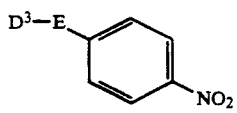

(XXI)

wherein W, X, Y, Z, $A^1$, $A^2$ and E are as defined above, and $D^3$ represents a readily displaceable group.

Where compound XX is a triazole or tetrazole derivative, the anion thereof may be generated by carrying out the reaction in a base such as triethylamine. Where compound XX is an imidazole derivative, the anion thereof may conveniently be generated if the reaction is carried out in sodium hydride using N,N-dimethylformamide as solvent. Where salts of the compounds of formula XX are commercially available, e.g. the sodium salt of 1,2,4-triazole, these are advantageously utilised in N,N-dimethylformamide solution in place of the compounds of formula XX themselves, with no requirement in this instance for additional base to be present in the reaction mixture.

The readily displaceable group $D^3$ in the compounds of formula XXI is suitably a halogen atom, preferably bromine; except when the moiety $D^3$ is attached directly to the aromatic ring, i.e. when E represents a bond, in which case $D^3$ is preferably fluorine.

Where they are not commercially available, the nitro compounds of formula XXI above may be prepared by procedures analogous to those described in the accompanying Examples, or by methods well known from the art.

In an alternative approach to the 1,2,4-triazole derivatives, the nitro compounds of formula XIX may be prepared from those of formula X above by appropriate modification of the moiety Q using, for example, methods analogous to those described above with reference to the compounds of formulae III and IV. Thus, for example, since Q in the compounds of formula X represents a reactive carboxylate moiety, the compounds of formula XIX may be prepared therefrom by reaction with a compound of formula $A^2$—C(=$NNHA^1$)$NH_2$ or $A^2$—C(=$NNH_2$)$NHA^1$.

In a still further process, the compounds according to the invention wherein the group F is an indazole moiety of structure FB as defined above may be prepared by a method which comprises cyclising a compound of formula XXII:

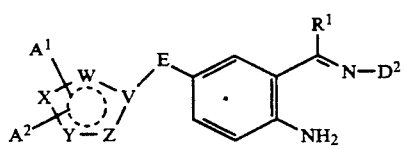

(XXII)

wherein V, W, X, Y, Z, $A^1$, $A^2$, E, $R^1$ and $D^2$ are as defined above; followed, where required, by N-alkylation by standard methods to introduce the moiety $R^3$.

As with the cyclisation of compound XI, that of compound XXII is conveniently achieved in a suitable organic solvent at an elevated temperature, for example in a mixture of m-xylene and 2,6-lutidine at a temperature in the region of 140° C.

The compounds of formula XXII may, for example, be prepared from the corresponding compound of formula XXIII:

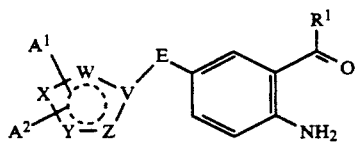

(XXIII)

wherein V, W, X, Y, Z, $A^1$, $A^2$, E and $R^1$ are as defined above; or a protected derivative thereof; which in turn may be prepared from the corresponding compound of formula XXIV:

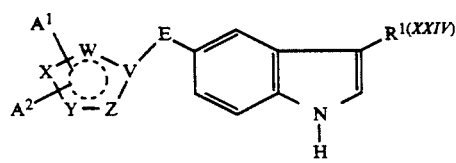

(XXIV)

wherein V, W, X, Y, Z, $A^1$, $A^2$, E and $R^1$ are as defined above; using methods analogous to those described above with reference to the compounds of formulae XII and XIII. Thus, for example, since Q in the compounds of formula XIII represents a reactive carboxylate moiety, the 1,2,4-triazole derivatives of formula XXIV may be prepared therefrom by reaction with a compound of formula $A^2$—C(=$NNHA^1$)$NH_2$ or $A^2$—C(=$NNH_2$)$NHA^1$.

In a yet further process, the compounds according to the invention wherein the group F is a benzofuran or benzthiophene moiety may be prepared by a method which comprises cyclising a compound of formula XXV:

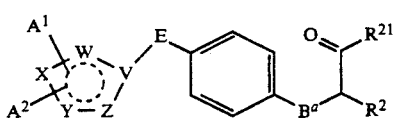

(XXV)

wherein V, W, X, Y, Z, $A^1$, $A^2$, E and $R^2$ are as defined above, $B^a$ represents oxygen or sulphur, and $R^{21}$ corresponds to the group $R^1$ as defined above or represents a precursor group thereto as discussed below; followed, where required, by conversion of the group $R^{21}$ into the desired group $R^1$ by conventional means.

The cyclisation is conveniently effected by using polyphosphoric acid or a polyphosphate ester, advantageously at an elevated temperature.

The compounds of formula XXV may be prepared by reacting a compound of formula XXVI with a compound of formula XXVII:

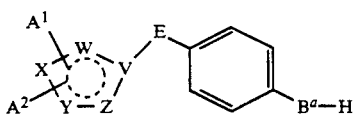

(XXVI)

-continued

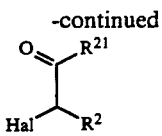

wherein V, W, X, Y, Z, $A^1$, $A^2$, E, $B^a$, $R^2$ and $R^{21}$ are as defined above, and Hal represents halogen.

The reaction is conveniently effected in the presence of a base such as sodium hydroxide.

The hydroxy and mercapto derivatives of formula XXVI may be prepared by a variety of methods which will be readily apparent to those skilled in the art. In one such method, the anion of a compound of formula XX as defined above is reacted with a compound of formula XXVIII:

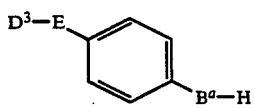

wherein $D^3$, E and $B^a$ are as defined above; to afford an intermediate of formula XXVI wherein V is nitrogen.

The compounds of formula XXVII and XXVIII, where they are not commercially available, may be prepared by standard procedures well known in the art.

It will be understood that any compound of formula I initially obtained from any of the above processes may, where appropriate, subsequently be elaborated into a further compound of formula I by techniques known from the art. Indeed, as will be appreciated, the compound of formula XV above in which $R^d$ is a group of formula -E-F is itself a compound of formual I in which $A^1$ is hydrogen and $A^2$ represents a non-bonded electron pair. In particular, a compound of formula I wherein $R^3$ is hydrogen initially obtained may be converted into a compound of formula I wherein $R^3$ represents $C_{1-6}$ alkyl, $C_{2-6}$ alkenyl or $C_{2-6}$ alknyl by standard techniques such as alkylation, for example by treatment with an alkyl iodide, e.g. methyl iodide, typically under basic conditions, e.g. sodium hydride in dimethylformamide, or triethylamine in acetonitrile. Similarly, a compound of formula I wherein $R^1$ represents a group of formula $-CH_2.CHR^4.NH_2$ initially obtained may be converted into a compound of formula I wherein $R^1$ represents a group of formula $-CH_2.CHR^4.NR^6R^7$ in which $R^6$ and $R^7$ are as defined above with the exception of hydrogen, for example by conventional N-alkylation or N-arylation techniques, e.g. by treatment with the appropriate aldehyde in the presence of a reducing agent such as sodium cyanoborohydride.

Where the above-described processes for the preparation of the compounds according to the invention give rise to mixtures of stereoisomers, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley and Sons, 1981. The protecting groups may be removed at a convenient subsequent stage using methods known from the art.

Alternatively, certain of the functional groups on the desired products may be carried through the reaction sequence as precursor groups, and then regenerated from these precursor groups at a late stage in the overall synthesis. For example, where $R^1$ in the desired compound of formula I represents a group of formula $-(CH_2)_2NH_2$, this group can be generated from a cyano precursor $-CH_2CN$ by reduction using, for example, borane/tetrahydrofuran. The cyano precursor may in turn be carried through the reaction sequence as a methyl group $-CH_3$, which may conveniently be converted to $-CH_2CN$ by treatment with N-bromosuccinimide and benzoyl peroxide, in the presence of a bright light source, followed by reaction of the resulting bromo intermediate with sodium cyanide in dimethyl sulphoxide.

The following Examples illustrate the preparation of compounds according to the invention.

The ability of test compounds to bind to 5-$HT_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and mesulergine (100 nM) were included in the assay to block out 5-$HT_{1A}$ and 5-$HT_{1C}$ binding sites respectively. The concentration of the compounds of the accompanying Examples required to displace 50% of the specific binding ($IC_{50}$) is below 1 μM in each case.

The activity of test compounds as agonists of the 5-$HT_1$-like receptor was measured in terms of their ability to mediate contraction of the saphenous vein of New Zealand White rabbits, using the procedure described in *Arch. Pharm.*, 1990, 342, 111. Agonist potencies were calculated as $-\log_{10}EC_{50}$ ($pEC_{50}$) values, from plots of percentage 5-HT (1 μm) response against the concentration of the agonist. The compounds of the accompanying Examples were found to possess $pEC_{50}$ values in this assay of not less than 5.0 in each case.

EXAMPLE 1

2-[5-(2-Benzyltetrazol-5-ylmethyl)-1H-indol-3-yl]ethylamine. Oxalate 1. 4-Hydrazinobenzylcyanide. Hydrochloride A solution of $NaNO_2$ (80 g, 1.16 mol) was added dropwise to a cooled (−10° C.), stirred, suspension of 4-aminobenzyl cyanide (153.5 g, 1.16 mol) in concentrated HCl (1500 ml), at such a rate that the temperature did not rise above −10° C. The mixture was stirred at −10° C. for 0.25 h before being filtered rapidly under vacuum into an addition funnel. The solution was added portionwise over a 0.25 h period to a rapidly stirred mixture of $SnCl_2.2H_2O$ (1.05 kg, 4.64 mol) in concentrated HCl (800 ml) keeping the temperature below −5°

C. The mixture was allowed to warm to room temperature and stir for 0.25 h before filtering the sandy coloured precipitate under vacuum and washing with ether (5×500 ml). The resultant solid was dried over P$_2$O$_5$ in a vacuum oven (80° C.) for 16 h to give the title compound (213 g, 100%), m.p. 181°–183° C.; $^1$H NMR (360 MHz, D$_2$O) δ 3.90 (2H, s, CH$_2$); 7.06 (2H, d, J=8.7 Hz, Ar-H); 7.40 (2H, d, J=8.7 Hz, Ar-H).

2. 2-(5-Cyanomethyl-1H-indol-3-yl)ethylamine. Hydrochloride

4-Chlorobutanal dimethylacetal (37.07 g, 0.24 mol) was added to a stirred solution of 4-hydrazinobenzyl cyanide hydrochloride (47.0 g, 0.26 mol) in EtOH/H$_2$O (5:1; 21) and refluxed for 4.5 h. The reaction mixture was evaporated to dryness under vacuum, MeOH (150 ml) added, and the mixture left at 0° C. for 10 h. The resultant pale yellow precipitate was filtered under vacuum, washed with Et$_2$O/MeOH (5:1; 2×100 ml) and dried. The product was used without further purification (24.1 g, 40%), m.p. 239°–241° C.; R$_f$ 0.4 in CH$_2$Cl$_2$/EtOH/NH$_3$ (40:8:1); $^1$H NMR (360 MHz, D$_2$O) 3.18 (2H, t, J=7.1 Hz, CH$_2$); 3.36 (2H, t, J=7.1 Hz, CH$_2$); 4.02 (2H, s, CH$_2$); 7.22 (1H, dd, J=1.5 and 8.4 Hz, Ar-H); 7.36 (1H, s, Ar-H); 7.56 (1H, d, J=8.4 Hz, Ar-H); 7.66 (1H, s, Ar-H).

3. 2-(5-Tetrazol-5-ylmethyl-1H-indol-3-yl) ethylamine

A solution of 2-(5-cyanomethyl-1H-indol-3-yl)ethylamine hydrochloride (2.5 g, 10.6 mmol), triethylamine hydrochloride (2.2 g, 16.0 mmol) and sodium azide (2.1 g, 32.3 mmol), in 1-methylpyrrolidin-2-one (30 ml) was heated at 140° C. for 8 h. 5N hydrochloric acid (3 ml) was added and the solvents removed by distillation under vacuum. The residue was chromatographed on silica-gel eluting with EtOH/Et$_2$O/H$_2$O/NH$_3$ (20:30:8:1) to give the title-tetrazole (1.76 g, 69%); δ (360 MHz, CD$_3$OD) 3.06 (2H, t, J=7.2 Hz, CH$_2$); 3.19 (2H, t, J=7.2 Hz, CH$_2$); 4.29 (2H, s, CH$_2$); 7.07 (1H, d, J=8.4 Hz, Ar-H); 7.13 (1H, s, Ar-H); 7.29 (1H, d, J=8.4 Hz, Ar-H); 7.44 (1H, s, Ar-H).

4. N-tert-Butyloxycarbonyl-2-(5-tetrazol-5-ylmethyl-1H-indol-3-yl)ethylamine

To a stirred suspension of 2-(5-tetrazol-5-ylmethyl-1H-indol-3-yl)ethylamine (1.76 g, 7.27 mmol) in dry CH$_2$Cl$_2$ (40 ml) was added triethylamine (1.5 g, 14.9 mmol) and (BOC)$_2$O (1.9 g, 7.3 mmol) and the mixture stirred for 16 h. The solvent was removed under vacuum and the residue chromatographed on silica-gel eluting with EtOH/Et$_2$O/H$_2$O/NH$_3$ (20:60:8:1) to give the title product (1.6 g, 64%); δ (360 MHz, CD$_3$OD) 1.41 (9H, s, 3 of CH$_3$); 2.87 (2H, t, J=7.4 Hz, CH$_2$); 3.30 (2H, t, J=7.4 Hz, CH$_2$); 4.32 (2H, s, CH$_2$); 6.99 (1H, d, J=8.3 Hz, Ar-H); 7.04 (1H, s, Ar-H); 7.26 (1H, d, J=8.3 Hz, Ar-H); 7.49 (1H, s, Ar-H).

5. N-tert-Butyloxycarbonyl-2-[5-(2-benzyltetrazol-5-ylmethyl)-1H-indol-3-yl]ethylamine and N-tert-butyloxycarbonyl-2-[5-(1-benzyltetrazol-5-ylmethyl)-1H-indol-3-yl]ethylamine Benzyl bromide (0.31 g, 1.8 mmol) was added to a solution of the tetrazole from step 4 (0.62 g, 1.8 mmol) and triethylamine (0.37 g, 3.6 mmol) in dry acetonitrile (20 ml). The mixture was stirred at R.T. for 2 h, heated at 70° C. for 1 h and then stirred at R.T. for 16 h. The solvent was removed under vacuum and the residue chromatographed through silica-gel eluting with CH$_2$Cl$_2$/MeOH (97:3) to give 2-separated benzyl tetrazoles. The less polar isomer was identified as the 2-benzyl tetrazole (0.17 g, 22.4%); δ (360 MHz, CDCl$_3$) 1.43 (9H, s, 3 of CH$_3$); 2.90 (2H, t, J=6.8 Hz, CH$_2$); 3.41 (2H, br t, CH$_2$); 4.32 (2H, s, CH$_2$); 5.70 (2H, s, CH$_2$Ph); 7.00 (1H, s, Ar-H); 7.15 (1H, d, J=8.4 Hz, Ar-H); 7.28 (1H, d, J=8.4 Hz, Ar-H); 7.34 (5H, s, Ar-H); 7.50 (1H, s, Ar-H); 7.96 (1H, br s, NH).

The more polar component was identified as the 1-benzyltetrazole (0.2 g, 26.4%) δ (360 MHz, CDCl$_3$) 1.43 (9H, s, 3 of CH$_3$); 2.88 (2H, t, J=7.0 Hz, CH$_2$); 3.40 (1H, br t, CH$_2$); 4.26 (2H, s, CH$_2$); 5.29 (2H, s, CH$_2$-Ph); 6.92 (1H, d, J=8.4 Hz, Ar-H); 7.01–7.05 (3H, m, Ar-H); 7.27–7.30 (5H, m, Ar-H); 8.08 (1H, br s, NH).

6. 2-[5-(2-Benzyltetrazol-5-ylmethyl)-1H-indol-3-yl]ethylamine. Oxalate

Trifluoroacetic acid (1.5 ml) was added to a solution of the less polar component isolated from step 5 (0.17 g, 0.4 mmol) in CH$_2$Cl$_2$ (5 ml) and stirred at R.T. for 1 h. The solvents were removed under vacuum and the residue chromatographed through silica-gel eluting with CH$_2$Cl$_2$/EtOH/NH$_3$ (40:8:1) to give the title-tetrazole. The oxalate salt was prepared (65 mg); mp 169°–171° C.; (Found: C, 59.23; H, 5.07; N, 19.60. C$_{19}$H$_{20}$N$_6$.1.05 (C$_2$H$_2$O$_4$) requires C, 59.36; H, 5.22; N, 19.68%); δ (360 MHz, D$_2$O) 3.09 (2H, t, J=6.9 Hz, CH$_2$); 3.29 (2H, t, J=6.9 Hz, CH$_2$); 4.30 (2H, s, CH$_2$); 5.77 (2H, s, CH$_2$); 7.11 (1H, dd, J=1.6 and 8.4 Hz, Ar-H); 7.28 (1H, s, Ar-H); 7.32–7.34 and 7.39–7.41 (5H, m, Ar-H); 7.43 (1H, d, J=8.4 Hz, Ar-H); 7.51 (1H, s, Ar-H).

EXAMPLE 2

2-[5-(1-Benzyltetrazol-5-ylmethyl)-1H-indol-3-yl]ethylamine. Hydrochloride. Hemihydrate Prepared from the more polar component isolated from step 5, Example 1, using the procedure described for step 6, Example 1. The hydrochloride hemihydrate salt was prepared; mp 210°–213° C.; (Found: C, 60.39; H, 5.88; N, 22.14. C$_{19}$H$_{20}$N$_6$.HCl.0.5H$_2$O requires C, 60.39; H, 5.87; N, 22.24%); δ (250 MHz, D$_2$O) 3.02 (2H, t, J=6.8 Hz, CH$_2$); 3.19 (2H, t, J=6.8 Hz, CH$_2$); 4.44 (2H, s, CH$_2$); 5.60 (2H, s, CH$_2$); 6.95–7.02 (3H, m, Ar-H); 7.16–7.25 (4H, m, Ar-H); 7.28 (1H, s, Ar-H); 7.40 (1H, d, J=8.4 Hz, Ar-H).

EXAMPLE 3

N,N-Dimethyl-2-[5-(2-methyltetrazol-5-ylmethyl)-1H-indol-3-yl]ethylamine. Oxalate 1. N-tert-Butyloxycarbonyl-2-[5-(2-methyltetrazol-5-ylmethyl)-1H-indol-3-yl]ethylamine and N-tert-butyloxycarbonyl-2-[5-(1methtetrazol-5-ylmethyl)-1H-indol-3-yl]ethylamine Methyl iodide (0.44 g, 3.1 mmol) was added to a stirred solution of the tetrazole from step 4, Example 1 (0.95 g, 2.78 mmol) and triethylamine (0.56 g, 5.5 mmol) in dry acetonitrile (15 ml). After 10 h a further equivalent of methyl iodide was added and stirred for 16 h. The solvent was removed under vacuum and the residue chromatographed on silica-gel eluting with CH$_2$Cl$_2$/MeOH (97:3) to give the title mixture of 1- and 2-methyltetrazoles (0.6 g, 61%); δ (360 MHz, CDCl$_3$) 1.43 (9H, m, 3 of CH$_3$); 2.89–2.92 (2H, m, CH$_2$); 3.38–3.48 (2H, m, CH$_2$); 3.83 (2H, s, CH$_2$); 4.28 and 4.40 (total 3H, s, CH$_3$); 6.98 and 7.17 (total 1H, d, J=8.4 Hz, Ar-H); 7.02 and 7.06 (total 1H, s, Ar-H); 7.30 and 7.31 (total 1H, d, J=8.4 Hz, Ar-H); 7.43 and 7.54 (total 1H, s, Ar-H); 8.00 and 8.10 (total 1H, br s, NH).

2. 2-[5-(2-Methyltetrazol-5-ylmethyl)-1H-indol-3-yl]ethylamine and 2-[5-(1-methyltetrazol-5-ylmethyl)-1H-indol-3-yl]ethylamine Prepared from the preceding methyltetrazoles using the procedure described in step 6, Example 1. The crude product was chromatographed on silica-gel eluting with $CH_2Cl_2/EtOH/NH_3$ (40:8:1) to give 2 separated components. The less polar product (0.1 g, 24%) was identified as the 2-methyltetrazole; δ (360 MHz, $CDCl_3$) 1.38 (9H, s, 3 of $CH_3$); 2.88 (2H, t, J=6.6 Hz, $CH_2$); 3.00 (2H, t, J=6.6 Hz, $CH_2$); 4.28 (3H, s, $CH_3$); 4.33 (2H, s, $CH_2$); 7.00 (1H, d, J=8.4 Hz, Ar-H); 7.06 (1H, d, J=2.1 Hz, Ar-H); 7.17 (1H, d, J=8.4 Hz, Ar-H); 7.56 (1H, s, Ar-H); 8.04 (1H, br s, NH).

The more polar product (0.13 g, 31%) was identified as the 1-methyltetrazole; δ (360 MHz, $CDCl_3$) 1.38 (9H, s, 3 of $CH_3$); 2.86 (2H, t, J=6.6 Hz, $CH_2$); 3.00 (2H, t, J=6.6 Hz, $CH_2$); 3.82 (3H, s, $CH_3$); 4.40 (2H, s, $CH_2$); 6.98 (1H, dd, J=1.6 and 8.3 Hz, Ar-H); 7.06 (1H, d, J=1.6 Hz, Ar-H); 7.31 (1H, d, J=8.3 Hz, Ar-H); 7.41 (1H, s, Ar-H); 8.18 (1H, br s, NH).

3. N,N-Dimethyl-2-[5-(2-methyltetrazol-5-ylmethyl)-1H-indol-3-yl]ethylamine. Oxalate A solution of formaldehyde (80 mg of a 30% solution) in methanol (15 ml) was added to a stirred solution of 2-[5-(2-methyltetrazol-5-ylmethyl)-1H-indol-3-yl]ethylamine (0.1 g, 0.4 mmol), $NaCNBH_3$ (60 mg) and glacial acetic acid (0.12 g) in methanol (15 ml). The solution was stirred for 2 h, basified with $K_2CO_3$ solution and the MeOH removed under vacuum. The crude product obtained after extraction into ethylacetate and removal of solvent was chromatographed through silica-gel eluting with $CH_2Cl_2/EtOH/NH_3$ (40:8:1) to give the desired N,N-dimethyltryptamine (96 mg, 87%). The oxalate salt was prepared: mp 185°-187° C. (MeOH-/$Et_2O$); (Found: C, 54.42; H, 5.74; N, 22.53. $C_{15}H_{20}N_6.C_2H_2O_4$ requires C, 54.54; H, 5.92; N, 22.45%); δ (360 MHz, $D_2O$) 2.91 (6H, s, 2 of $CH_3$); 3.21 (2H, t, J=7.4 Hz, $CH_2$); 3.47 (2H, J=7.4 Hz, $CH_2$); 4.30 (3H, s, $CH_3$); 4.34 (2H, s, $CH_2$); 7.17 (1H, dd, J=1.5 and 8.4 Hz, Ar-H); 7.33 (1H, s, Ar-H); 7.48 (1H, d, J=8.4 Hz, Ar-H); 7.59 (1H, s, Ar-H).

EXAMPLE 4

N,N-Dimethyl-2-[5-(1-methyltetrazol-5-ylmethyl)-1H-indol-3-yl]ethylamine. Oxalate Prepared from 2-[5-(1-methyltetrazol-5-ylmethyl)-1H-indol-3-yl]ethylamine (0.125 g, 0.49 mmol) using the procedure described in step 3, Example 3. The free base (0.11 g, 80%) obtained was converted to the oxalate salt and recrystallised from MeOH/$Et_2O$; mp 176°-177° C.; (Found: C, 54.21; H, 5.84; N, 22.36. $C_{15}H_{20}N_6 \cdot C_2H_2O_4$ requires C, 54.54; H, 5.92; N, 22.45%); δ (360 MHz, $D_2O$); 2.91 (6H, s, 2 of $CH_3$); 3.21 (2H, t, J=7.4 Hz, $CH_2$); 3.40 (2H, t, J=7.4 Hz, $CH_2$); 4.00 (3H, s, $CH_3$); 4.43 (2H, s, $CH_2$); 7.13 (1H, dd, J=1.5 and 8.4 Hz, Ar-H); 7.35 (1H, s, Ar-H); 7.50 (1H, d, J=8.4 Hz, Ar-H); 7.54 (1H, s, Ar-H).

EXAMPLE 5

N,N-Dimethyl-2-[5-(1,2,4-triazol-1-ylmethyl)-1H-indol-3-yl]ethylamine. Oxalate Hemihydrate 1. 1-(4-Nitrophenyl)methyl-1,2,4-triazole 4-Nitrobenzylbromide (21.6 g, 0.1 mol) was added to a rapidly stirred suspension of 1,2,4-triazole sodium salt (9.1 g, 0.1 mol) in anhydrous DMF (100 ml) and the mixture stirred at room temperature for 16 h. Ethyl acetate (400 ml) was added followed by water (250 ml) and the layers separated. The organic phase was washed with water (3×250 ml), dried ($MgSO_4$) and evaporated. The residue was chromatographed on silica gel eluting with ethyl acetate to give the title-product (10.6 g, 52%); m.p. 98°-100° C. δ (360 MHz, $CDCl_3$) 5.47 (2H, s, $CH_2$) 7.40 (2H, d, J=9 Hz, Ar-H), 8.02 (1H, s, Ar-H), 8.18 (1H, s, Ar-H), 8.23 (2H, d, J=9 Hz, Ar-H).

2. 1-(4-Aminophenyl)methyl-1,2,4-triazole. Hydrochloride

A solution of 1-(4-nitrophenyl)methyl-1,2,4-triazole (10.0 g, 49 mmol) in ethanol (50 ml), ethyl acetate (50 ml), 5N HCl (10 ml) and water (10 ml) was hydrogenated over 10% Pd/C (1.0 g) at 40 p.s.i., in a Parr apparatus, until an uptake of 188 p.s.i., had been observed (approx 10 mins). The catalyst was removed by filtration through hyflo and the solvent removed under vacuum. The residue was azeotroped with ethanol (×2) to give the titleamine hydrochloride (10.6 g, 100%). δ (360 MHz, $D_2O$) 5.53 (2H, s, $CH_2$), 7.37-7.48 (4H, m, Ar-H), 8.12 (1H, s, Ar-H), 8.66 (1H, s, Ar-H).

3. 1-(4-Hydrazinophenyl)methyl-1,2,4-triazole

A solution of sodium nitrite (3.28 g, 48 mmol) in water (20 ml) was added to a solution of the preceding amine hydrochloride (10.0 g, 48 mmol), in concentrated HCl (40 ml), at such a rate that the temperature did not exceed −10° C. After addition was complete the solution was stirred at 0° C. for 0.25 h and then added portionwise to a rapidly stirred solution of $SnCl_2.2H_2O$ (40 g) in concentrated HCl (40 ml). The solution was warmed to room temperature and basified with 20% aqueous NaOH solution. The solution was extracted with ethyl acetate (3×250 ml) and the combined extracts dried ($MgSO_4$) and filtered through hyflo. The solution was evaporated to dryness to give the desired hydrazine (5.0 g, 56%) m.p. 109°-112° C. δ (360 MHz, $D_6$-DMSO) 3.93 (2H, br s, $NH_2$), 5.20 (2H, s, $CH_2$), 6.73 (2H, d, J=8 Hz, Ar-H), 7.08 (2H, d, J=8 Hz, Ar-H), 7.92 (1H, s, Ar-H), 8.57 (1H, s, Ar-H).

4. 2-[5-(1,2,4-Triazol-1-ylmethyl)-1H-indol-3-yl]ethylamine.

4-Chlorobutanal dimethylacetal (3.22 g, 21.1 mmol) was added to a stirred solution of the preceding hydrazine (5.0 g, 26.4 mmol) in ethanol/water (5:1, 180 ml) and 5N HCl (4.5 ml) and the solution refluxed for 4 h. The solvents were removed under vacuum and the residue chromatographed on silica gel, eluting with $CH_2Cl_2/EtOH/NH_3$ (30:8:1) to give the desired tryptamine (2.4 g, 38%). δ(360 MHz, $CDCl_3$) 2.90 (2H, t, J=7 Hz, $CH_2$), 2.99 (2H, t, J=7 Hz, $CH_2$), 5.43 (2H, s, $CH_2$), 7.10 (1H, s, Ar-H), 7.11 (1H, d, J=8Hz, Ar-H), 7.39 (1H, d, J=8Hz, Ar-H), 7.57 (1H, s, Ar-H), 7.94 (1H, s, Ar-H), 8.08 (1H, s, Ar-H).

5. N,N-Dimethyl-2-[5-(1,2,4-triazol-1-ylmethyl)-1H-indol-3-yl]ethylamine Oxalate Hemihydrate A solution of formaldehyde (37% w/w solution, 0.19 g), in methanol (10 ml), was added to a mixture of the preceding tryptamine (0.36 g, 1.5 mmol), $NaCNBH_3$ (0.225 g, 3.6 mmol) and glacial acetic acid (0.45 g), in methanol (10 ml). The mixture was stirred at room temperature for 2 h before adding saturated $K_2CO_3$ (50 ml) and evaporating the methanol. The residue was extracted with ethyl acetate (3×100 ml) and the combined extracts washed with brine (100 ml), dried ($K_2CO_3$), and evaporated. The crude product was chromatographed on silica gel eluting with $CH_2Cl_2/EtOH/NH_3$ (20:8:1) to give the free base of the title-compound (0.21 g, 52%). The oxalate hemihydrate salt was prepared, m.p. 165°-167° C. (MeOH/Et$_2$O); (Found: C, 55.53; H, 6.04; N, 18.59. C$_{15}$H$_{19}$N$_5$.C$_2$H$_2$O$_4$. 0.5H$_2$O requires C, 55.29; H, 6.03; N, 18.96%); m/e 269 (M$^+$); δ (360 MHz, D$_2$O) 2.91 (6H, s, NMe$_2$), 3.22 (2H, t, J=7 Hz, CH$_2$), 3.47 (2H, t, J=7 Hz, CH$_2$), 5.52 (2H, s, CH$_2$), 7.21 (1H, dd, J=1.6 and 8.4 Hz, Ar-H), 7.36 (1H, s, Ar-H), 7.52 (1H, d, J=8.4 Hz, Ar-H), 7.65 (1H, s, Ar-H), 8.06 (1H, s, Ar-H), 8.56 (1H, s, Ar-H).

EXAMPLE 6

N,N-Dimethyl-2-[5-(1,2,3,4-tetrazol-2-ylmethyl)-1H-indol-3-yl]ethylamine Oxalate.

1. 1-(4-Nitrophenyl)methyl-1,2,3,4-tetrazole and 2-(4-nitrophenyl)methyl-1,2,3,4-tetrazole.

4-Nitrobenzylbromide (15.42 g, 71.3 mmol) was added to a stirred solution of 1H-tetrazole (5.0 g, 71.3 mmol) and triethylamine (7.9 g, 78.0 mmol) in acetonitrile (100 ml). The mixture was stirred at room temperature for 16 h, the solvent removed under vacuum and the residue chromatographed on silica gel eluting with dichloromethane to give 2-isomers. The 2-alkylated product was obtained as the less polar product (2.47 g, 17%); δ (360 MHz, CDCl$_3$) 5.92 (2H, s, CH$_2$), 7.53 (2H, d, J=8.7 Hz, Ar-H), 8.25 (2H, d, J=8.7 Hz, Ar-H), 8.56 (1H, s, Ar-H). The more polar, major isomer was identified as the 1-alkylation product (11 g, 75%); δ (360 MHz, CDCl$_3$) 5.73 (2H, s, CH$_2$), 7.46 (2H, d, J=8.7 Hz, Ar-H), 8.27 (2H, d, J=8.7 Hz, Ar-H), 8.64 (1H, s, Ar-H).

2. 2-(4-Aminophenyl)methyl-1,2,3,4-tetrazole. Hydrochloride 2-(4-Nitrophenyl)methyl-1,2,3,4-tetrazole (2.47 g, 12.1 mmol) was hydrogenated as described for Example 5 step 2. The product (2.55 g, 100%) was obtained as the hydrochloride salt; δ (250 MHz, D$_2$O) 5.86 (2H, s, CH$_2$), 7.40 (2H, d, J=8.7 Hz, Ar-H), 7.36 (2H, d, J=8.7 Hz, Ar-H), 8.74 (1H, s, Ar-H).

3. N,N-Dimethyl-2-[5-(1,2,3,4-tetrazol-2-ylmethyl)-1H-indol-3-yl]ethylamine. Oxalate.

The preceding amine was converted into the title-compound using the general procedures described for Example 5 Steps 3-5. The oxalate salt was prepared and recrystallised from MeOH/Et$_2$O; mp 198°-199° C.; (Found: C, 53.38; H, 5.55; N, 22.63. C$_{14}$H$_{18}$N$_6$.C$_2$H$_2$O$_4$.0.2 (EtOH) requires C, 53.30; H, 5.78; N, 22.74%); δ(360 MHz, D$_2$O) 2.91 (6H, s, NMe$_2$), 3.23 (2H, t, J=7.4 Hz, CH$_2$), 3.48 (2H, t, J=7.4 Hz, CH$_2$), 6.01 (2H, s, CH$_2$), 7.30 (1H, dd, J=1.6 and 8.4 Hz, Ar-H), 7.37 (1H, s, Ar-H), 7.53 (1H, d, J=8.4 Hz, Ar-H), 7.76 (1H, s, Ar-H), 8.74 (1H, s, Ar-H).

EXAMPLE 7

N,N-Dimethyl-2-[5-1,2,3,4-tetrazol-1-ylmethyl)-1H-indol-3-yl]ethylamine. Succinate 1-(4-nitrophenyl)methyl-1,2,3,4-tetrazole was converted into the title-compound using the procedures described for Example 5. The succinate salt was prepared, m.p. 55°-56° C. (isopropylalcohol); (Found C: 57.08; H, 6.14; N, 23.34. C$_{14}$H$_{18}$N$_6$.0.75 (C$_4$H$_6$O$_4$) requires C, 56.89; H, 6.32; N, 23.42%); δ (360 MHz,D$_2$O) 2.93 (6H, s, NMe$_2$), 3.23 (2H, t, J=7.5 Hz, CH$_2$), 3.48 (2H, t, J=7.5 Hz, CH$_2$), 5.81 (2H, s, CH$_2$), 7.28 (1H, dd, J=1.7 and 8.4 Hz, Ar-H), 7.39 (1H, s, Ar-H), 7.56 (1H, d, J=8.4 Hz, Ar-H), 7.75 (1H, s, Ar-H), 9.20 (1H, s, Ar-H).

EXAMPLE 8

N,N-Dimethyl-2-[5-(1-methyl-1,2,4-triazol-5-ylmethyl)-1H-indol-3-yl]ethylamine. Bisoxalate 1. Ethyl 3-[2-(dimethylamino)ethyl]-1H-indole-5-methylcarboximidate. Hydrochloride A solution of N,N-dimethyl-2-(5-cyanomethyl-1H-indol-3-yl)ethylamine (5 g, 22.01 mmol) in ethanol was saturated with HCl gas and the solution stirred at room temperature for 16 h. The solvent was removed under vacuum to give the title-product (6 g, 92%); δ (360 MHz, D$_6$-DMSO) 1.29 (3H, t, J=7.0 Hz, CH$_2$); 2.83 (6H, s, NMe$_2$), 3.13 (2H, t, J=7.5 Hz, CH$_2$), 3.31 (2H, m, CH$_2$), 4.04 (2H, s, CH$_2$), 4.42 (2H, q, J=7.0 Hz, CH$_2$), 7.08 (1H, dd, J=1.5 and 8.4 Hz, Ar-H), 7.27 (1H, s, Ar-H), 7.37 (1H, d, J=8.4 Hz, Ar-H), 7.48 (1H, br s, NH), 7.71 (1H, s, Ar-H).

2. N,N-Dimethyl-2-[5-(1-methyl-1,2,4-triazol-5-ylmethyl)-1H-indol-3-yl]ethylamine. Bisoxalate A mixture of the preceding imidate ester (3 g, 10.15 mmol), methylhydrazine (0.8 ml) and triethylamine (3.54 ml), in ethanol (30 ml), was stirred at room temperature for 3 h. The solvent was removed under vacuum and the resultant product dissolved in formic acid (98%, 3.3 ml) and the solution stirred for 0.5 h at room temperature and refluxed for 2 h. The solution was cooled to room temperature, poured into an aqueous solution of K$_2$CO$_3$ (75 ml) and extracted with ethyl acetate (4×200 ml). The combined extracts were dried (MgSO$_4$) and evaporated, and the residue chromatographed through silica gel eluting with CH$_2$Cl$_2$/EtOH/NH$_3$ (40:8:1) to give 2-components. The less polar isomer was identified as the title-1-methyl-1,2,4-triazole (360 mg). The bisoxalate salt was prepared; mp 135°-137° C.; (Found: C, 50.91; H, 5.38; N, 13.86. C$_{16}$H$_{21}$N$_5$. 0.25(ethanol) requires C, 50.70; H, 5.47; N, 14.08%); δ (360 MHz, D$_2$O) 2.91 (6H, s, NMe$_2$); 3.23 (2H, t, J=7.3 Hz, CH$_2$), 3.48 (2H, t, J=7.3 Hz, CH$_2$), 3.95 (3H, s, Me), 4.48 (2H, s, CH$_2$), 7.13 (1H, dd, J=1.5 and 8.4 Hz, Ar-H), 7.37 (1H, s, Ar-H), 7.53 (1H, d, J=8.4 Hz, Ar-H), 7.57 (1H, s, Ar-H), 8.32 (1H, s, Ar-H).

EXAMPLE 9

N,N-Dimethyl-2-[5-(1-methyl-1,2,4-triazol-3-ylmethyl)-1H-indol-3-yl]ethylamine. Trishydrochloride.

The more polar isomer obtained from Example 8 Step 2 was identified as the title-triazole (180 mg). The trishydrochloride salt was prepared, mp<40° C. (hygroscopic); Found: C, 49.80, H, 6.56; N, 16.69. C$_{16}$H$_{21}$N$_5$. 3HCl. 0.35 (Et$_2$O) requires C, 49.91; H, 6.62; N, 16.73%); δ (360 MHz, D$_2$O) 2.91 (6H, s, NMe$_2$); 3.23 (2H, t, J=7.4 Hz, CH$_2$), 3.49 (2H, t, J=7.4 Hz, CH$_2$), 3.95 (3H, s, Me), 4.27 (2H, s, CH$_2$), 7.17 (1H, dd, J=1.5 and 8.5 Hz, Ar-H), 7.34 (1H, s, Ar-H), 7.50 (1H, d, J=8.5 Hz, Ar-H), 7.60 (1H, s, Ar-H), 8.88 (1H, s, Ar-H).

EXAMPLE 10

N,N-Dimethyl-2-[5-(1,2,3-triazol-1-ylmethyl)-1H-indol-3-yl]ethylamine. Oxalate.

1. 1-(4-nitrophenyl)methyl-1,2,3-triazole

4-Nitrobenzylbromide (25.4 g, 0.12 mol) was added to a solution of 1H-1,2,3-triazole (8.12 g, 0.12 mol) and triethylamine (11.88 g, 0.12 mol) in anhydrous acetonitrile. The mixture was refluxed for 1 h, cooled to room temperature and the precipitated NEt$_3$. HBr filtered off.

The solvent was removed under vacuum and the residue chromatographed through silica gel eluting with $CH_2Cl_2$ (100) to $CH_2Cl_2/MeOH$ (95.5) to give 2-products. The more polar product was identified as the title-1-isomer (13 g, 54%); mp 114°-116° C. δ (250 MHz, $CDCl_3$) 5.72 (2H, s, $CH_2$), 7.38 (2H, d, J=9 Hz, Ar-H), 7.64 (1H, s, Ar-H), 7.78 (1H, s, Ar-H), 8.18 (2H, d, J=9 Hz, Ar-H). The less polar, minor isomer was identified as the 2-alkylation product (2.25 g, 9%), mp 112°-113° C. δ (250 MHz, $CDCl_3$) 5.72 (2H, s, $CH_2$), 7.40 (2H, d, J=9 Hz, Ar-H), 7.66 (2H, s, Ar-H), 8.18 (2H, d, J=9 Hz, Ar-H).

2. N,N-Dimethyl-2-[5-(1,2,3-triazol-1-ylmethyl)-1H-indol-3-yl]ethylamine. Oxalate 1-(4-nitrophenyl)methyl-1,2,3-triazole was converted into the title-indole using the general procedures described for example 5. The oxalate salt was prepared mp 210°-212° C., (Found: C, 55.88; H, 5.75; N, 18.69. $C_{15}H_{19}N_5$. 1.1($C_2H_2O_4$) 0.15$H_2O$ requires C, 55.67; H, 5.84; N, 18.87%), δ (360 MHz, $D_2O$). 2.90 (6H, s, $NMe_2$), 3.22 (2H, t, J=7.4 Hz, $CH_2$), 3.46 (2H, t, J=7.4 Hz, $CH_2$), 5.72 (2H, s, $CH_2$), 7.24 (1H, dd, J=1.6 and 8.4 Hz, Ar-H), 7.36 (1H, s, Ar-H), 7.52 (1H, d, J=8.4 Hz, Ar-H), 7.66 (1H, s, Ar-H), 7.79 (1H, s, Ar-H), 8.00 (1H, d, J=1 Hz, Ar-H)

EXAMPLE 11

3-(2-Aminoethyl)-5-(2-methyl-tetrazol-5-yl)benzo[b]thiophene. Oxalate.

Step 1
4-Bromophenylmercaptopropanone

To a stirred solution of 4-bromothiophenol (5.09 g, 26.9 mmol) in NaOH (1.08 g, 26.9 mmol) and water (32 ml) was added chloroacetone (2.17 ml, 27.3 mmol) and the mixture was stirred under nitrogen for 45 min before extracting with ether, washing with water, drying ($Na_2SO_4$) and evaporating in vacuo, leaving 6.89 g (100%) of the title compound as a white solid, δ ($CDCl_3$) 2.27 (3H, s), 3.65 (2H, s), 7.20 (2H, d, J=8.5 Hz), 7.41 (2H, d, J=8.5 Hz).

Step 2
5-Bromo-3-methyl benzo[b]]thiophene

To a gently refluxing mixture of polyphosphoric acid (4.47 g) and chlorobenzene (100 ml) was added 4-bromophenylmercaptopropanone (2.24 g, 9.14 mmol) portionwise over 1 h and the mixture was heated at reflux for 8 days. After cooling the organic phase was decanted off and the residue was decomposed with $H_2O$ (~100 ml), extracted with $CH_2Cl_2$ (2×75 ml), dried ($MgSO_4$) and combined with the decanted organic phase. This was evaporated in vacuo to leave 2.096 g of brown oil. Distillation on a Kugelröhr apparatus yielded 1.83 g (88%) of the title compound as a pale yellow liquid, bp 100°-110° C./0.35 mbar. δ ($CDCl_3$) 2.41 (3H, s), 7.10 (1H, s), 7.43 (1H, dd, J=8.5 and 1.9 Hz), 7.69 (1H, d, J=8.5 Hz), 7.64 (1H, d, J=1.9 Hz).

Step 3
5-Cyano-3-methyl benzo[b]thiophene

To copper (I) cyanide (0.569 g, 6.35 mmol) was added 5-bromo-3-methyl benzo[b]thiophene (1.179 g, 5.19 mmol) in N-methylpyrrolidinone (10 ml) and the mixture was stirred at 180°-190° C. for 17 h. This was then partitioned between ether (75 ml) and ammonia solution (75 ml). The ether layer was separated, washed with more ammonia solution (2×50 ml), dried ($Na_2SO_4$) and evaporated in vacuo to leave 0.81 g of an off-white solid. Chromatography on flash silica, eluting with 10% ethyl acetate/petroleum ether yielded 0.76 g (85%) of the title compound as a white solid. δ ($CDCl_3$) 2.47 (3H, s), 7.23 (1H, s), 7.55 (1H, dd, J=8.3 and 1.5 Hz), 7.93 (1H, d, J=8.4 Hz), 8.03 (1H, d, J=1.4 Hz).

Step 4
3-Methyl-5-(tetrazol-5-yl)-benzo[b]thiophene

To a solution of 5-cyano-3-methyl benzo[b]thiophene (0.194 g, 1.12 mmol) in N-methylpyrrolidinone (5 ml) under nitrogen was added triethylamine hydrochloride (0.231 g, 1.68 mmol) followed by sodium azide (0.234 g, 3.59 mmol) and the mixture was extracted with ether (4×50 ml). The combined ether extracts were dried ($MgSO_4$) and evaporated in vacuo to leave 0.78 g of a white solid. This was chromatographed on flash silica, eluting with $CH_2Cl_2/MeOH/NH_3$(aq) (40:8:1 to 30:8:1), to give 0.246 g (100%) of the title product as a white solid. δ (DMSO) 2.46 (3H, s), 7.41 (1H, s), 7.98 (1H, d, J=8.4 Hz), 8.03 (1H, dd, J=8.4 and 1.5 Hz), 8.36 (1H, d, J=0.9 Hz). m/z ($CI^-$, $NH_3$) 215 (M−H)$^-$, 160.

Step 5
3-Methyl-5-(2-methyltetrazol-5-yl)benzo[b]thiophene and 3-Methyl-5-(1-methyltetrazol-5-yl) benzo[b]thiophene To a mixture of 3-Methyl-5-(tetrazol-5-yl) benzo[b]thiophene (0.241 g, 1.12 mmol) in acetonitrile (5 ml) was added triethylamine (0.28 ml, 2.01 mmol), then iodomethane (0.486 ml, 7.81 mmol) followed by DMF (3 ml) until a clear solution formed. The solution was stirred overnight under nitrogen before evaporating in vacuo and partitioning the residue between water (50 ml) and ether (25 ml). The aqueous layer was separated and extracted with more ether (2×25 ml), the combined ether extracts were dried (Mg $SO_4$) and evaporated in vacuo to leave 0.241 g of yellow solid. Chromatography on flash silica, eluting with 25-40% ethyl acetate/petroleum ether gave 0.168 g (65%) of the 2-isomer of the title product as a white solid and 0.063 g (24%) of the 1-isomer of the title product as a white solid. 2-isomer δ ($CDCl_3$) 2.52 (3H, s), 4.42 (3H, s), 7.14 (1H, s), 7.94 (1H, d, J=8.4 Hz), 8.10 (1H, dd, J=8.4 and 1.5 Hz), 8.51 (1H, s). m/z ($CI^+$,$NH_3$) 231 (M+H)$^+$ 1-isomer δ ($CDCl_3$) 2.50 (3H, s), 4.22 (3H, s), 4.22 (3H, s), 7.23 (1H, s), 7.64 (1H, dd, J=8.3 and 1.5 Hz), 8.03 (1H, d, J=8.4 Hz), 8.12 (1H, d, J=1.6 Hz). m/z ($CI^+$,$NH_3$) 231 (M+H)$^+$, 202, 172.

Step 6
3-Cyanomethyl-5-(2-methyltetrazol-5-yl) benzo[b]thiophene

To a refluxing mixture of 3-methyl-5-(2-methyltetrazol-5-yl) benzo[b]thiophene (0.162 g, 0.703 mmol) and benzoyl peroxide (10.6 mg) in carbon tetrachloride (10 ml) irradiated with two desk lamps (2×60 W) was added N-bromosuccinimide (0.126 g, 0.707 mmol) in small portions. After the addition was complete the mixture was heated at reflux for a further 90 min, then filtered and the filtrate was evaporated in vacuo to leave an oil/solid mixture. Chromatography on flash silica, eluting with dichloromethane gave 0.161 g of crude 3-bromomethyl-5-(2-methyltetrazol-5-yl) benzo[b]thiophene as a colourless oil.

The crude 3-bromomethyl-5-(2-methyl-tetrazol-5-yl) benzo[b]thiophene (0.145 g) in DMSO (0.3 ml) was added to a mixture of sodium cyanide (29.9 mg, 0.61 mmol) in DMSO (0.2 ml) and the mixture was stirred at 100° C. for 2 h. After cooling, the mixture was poured into water (10 ml) and a brown solid was filtered off, washed with water and dried in a vacuum pistol to leave 73.5 mg. The filtrate was extracted with dichloromethane (3×30 ml) and the combined extracts were dried (Na$_2$SO$_4$) and evaporated in vacuo to leave 44.7 mg. This was combined with the original solid and chromatographed on flash silica, eluting with 20–50% ethyl acetate/petroleum ether to yield 61.5 mg (38%) of the title product as a white solid. δ (CDCl$_3$) 3.99 (2H, s), 4.43 (3H, s), 7.59 (1H, s), 8.00 (1H, d, J=8.5 Hz), 8.19 (1H, dd, J=8.5 and 1.5 Hz), 8.47 (1H, s).

Step 7

3-(2-Aminoethyl)-5-(2-methyl-tetrazol-5-yl)benzo[b]-thiophene. Oxalate.

To a solution of 3-cyanomethyl-5-(2-methyl-tetrazol-5-yl)benzo[b]thiophene (0.434 g, 1.70 mmol) in THF (16 ml) under nitrogen was added dropwise 1.0M borane-tetrahydrofuran complex in THF (5.10 ml, 5.10 mmol) and the mixture was heated at reflux for 6 h. After cooling in an ice-bath the mixture was quenched with 2N HCl (22 ml) and heated to reflux for 1 h. The THF was then removed in vacuo and the residue basified with 50% sodium hydroxide solution (4 ml) before extracting with dichloromethane (3×75 ml). The combined extracts were dried (K$_2$CO$_3$) and evaporated in vacuo to leave 0.45 g. Chromatography on flash silica eluting with CH$_2$Cl$_2$/MeOH/NH$_3$(aq) (60:8:1) gave 0.383 g (87%) of the title product as a white solid. The oxalate salt was prepared using oxalic acid in methanol/ether to give the title product oxalate as a white solid, m.p. 204°–209° C. Analysis found: C, 47.75; H, 4.28; N, 19.28%. Calcd for C$_{12}$H$_{13}$N$_5$S. 1.1 C$_2$H$_2$O$_4$: C, 47.59; H, 4.28; N, 19.54%. δ (DMSO) 3.17–3.21 (4H, m), 4.46 (3H, s), 7.72 (1H, s), 8.06 (1H, dd, J=8.4 and 1.4 Hz), 8.52(1H, s) m/z (CI+, NH$_3$) 260 (M+H)+, 230.

EXAMPLE 12

3-(2-Aminoethyl)-5-(1-methyltetrazol-5-yl)benzo[b]thiophene. Oxalate.

Step 1

3-Cyanomethyl-5-(1-methyltetrazol-5-yl)benzo[b]thiophene

Following the procedure of Example 11, Step 6, 0.666 g (2.89 mmol) 3-methyl-5-(1-methyltetrazol-5-yl)benzo[b]thiophene was reacted with 0.515 g (2.89 mmol) of N-bromosuccinimide and 38.1 mg of benzoyl peroxide in 30 ml of carbon-tetrachloride. The reaction mixture was evaporated in vacuo and chromatographed on flash silica, eluting with 0–3% methanol/dichloromethane to give 0.532 g of crude 3-bromo-5-(1-methyltetrazol-5-yl)benzo[b]thiophene.

The crude 3-bromo-5-(1-methyltetrazol-5-yl)benzo[b]thiophene (0.504 g) was reacted with 97.7 mg (1.99 mmol) of sodium cyanide in 1.5 ml of DMSO at 100° C. for 2 h. After cooling, the reaction mixture was poured into water (25 ml) and extracted with dichloromethane (6×50 ml). The combined extracts were dried (Na$_2$SO$_4$) and evaporated in vacuo to leave 0.37 g. Chromatography on flash silica, eluting with 30–60% ethyl acetate/petroleum ether yielded 28.0 mg (4%) of the title product. δ (CDCl$_3$) 4.00 (2H, s), 4.23 (3H, s), 7.63 (1H, s), 7.73 (1H, dd), 8.08 (1H, d), 8.15 (1H, d).

Step 2

3-(2-Aminoethyl)-5-(1-methyltetrazol-5-yl)benzo[b]-thiophene. Oxalate.

Following the procedure of Example 11, Step 7, 26.1 mg (0.102 mmol) of 3-cyanomethyl-5-(1-methyltetrazol-5-yl)benzo[b]thiophene in 2 ml of THF was reacted with 0.36 ml (0.36 mmol) of 1.0M borane-tetrahydrofuran complex in THF. Chromatography on flash silica, eluting with CH$_2$Cl$_2$/MeOH/NH$_3$(aq) (60:8:1) gave 17.7 mg (67%) of the title product as a colourless oil. The oxalate salt was prepared using oxalic acid in methanol/ether to give the title product oxalate as a white solid, m.p. 206°–212° C. Analysis found: C, 47.55; H, 4.05; N, 19.65%. Calcd for C$_{12}$H$_{13}$N$_5$S. 1.1 C$_2$H$_2$O$_4$: C, 47.59; H, 4.28; N, 19.54%. δ (D$_2$O) 3.32–3.35 (2H, m), 3.40–3.44 (2H, m), 4.22 (3H, s), 7.64 (1H, s), 7.73 (1H, d, J=8.4 Hz), 8.19 (1H, s), 8.22 (1H, d, 8.5 Hz).

EXAMPLE 13

3-[2-(N,N-Dimethylamino)ethyl]-5-(2-methyltetrazol-5-yl)benzo[b]thiophene. Oxalate.

To a mixture of -(2-aminoethyl)-5-(2-methyltetrazol-5-yl)benzo[b]thiophene (0.372 g, 1.43 mmol) and sodium cyanoborohydride (0.136 g, 2.15 mmol) in methanol (3 ml) and acetic acid (0.247 ml, 4.30 mmol) cooled in an ice bath was added 38% w/v formaldehyde solution (0.453 ml, 5.74 mmol) in methanol (3 ml) dropwise over 5 min and the mixture was stirred at room temperature for 3 h. After this time, saturated potassium carbonate solution (30 ml) was added and the mixture was extracted with ethyl acetate (3×50 ml). The combined extracts were evaporated in vacuo to leave 0.53 g. Chromatography on flash silica, eluting with 10–30% methanol/dichloromethane, gave 0.335 g (81%) of the title product as a colourless oil. The oxalate salt was prepared using oxalic acid in methanol/ether to give the title product oxalate as a white solid, m.p. 214°–218° C. Analysis found: C, 50.58; H, 4.80; N, 18.28%. Calcd for C$_{14}$H$_{17}$N$_5$S. C$_2$H$_2$O$_4$: C, 50.92; H, 5.07; N, 18.56%. δ (DMSO) 2.84 (6H, s), 3.30–3.42 (4H, m), 4.46 (3H, s), 7.69 (1H, s), 8.06 (1H, dd, J=8.4 and 1.4 Hz), 8.20 (1H, d, J= 8.4 Hz), 8.56 (1H, s). m/z (CI+,NH$_3$) 288 (M+H)+.

EXAMPLE 14

N,N-Dimethyl-2-[5-(2-methylimidazol-1-ylmethyl)-1H-indol-3-yl]ethylamine Trisoxalate 1. 1-(4-Nitrophenyl)methyl-2-methylimidazole Sodium hydride (2.45 g; 61.0 mmol, 60% dispersion in oil) was added to a solution of 2-methylimidazole (5.0 g, 60.9 mmol) in DMF (100 ml). The mixture was stirred at room temperature for 0.25 h before adding 4-nitrobenzyl bromide (13.2 g, 61.0 mmol) and heating at 110° C. for 2 h followed by stirring at room temperature for 16 h. Water (200 ml) and ethyl acetate (500 ml) were added, the aqueous separated and extracted with ethyl acetate (2×500 ml). The combined extracts were washed with water (3×250 ml), dried (MgSO$_4$) and evaporated. The crude product was chromatographed on silica gel eluting with CH$_2$Cl$_2$/MeOH (4%) to give the title-product (1.58 g, 10.5%); δ (360 MHz, CDCl$_3$) 2.34 (3H, s, Me); 5.16 (2H, s, CH$_2$); 6.67 (1H, d, J=1.3 Hz, Ar-H); 7.03 (1H, d, J=1.3 Hz, Ar-H); 7.19 (2H, d, J=9.5 Hz, Ar-H); 8.22 (2H, d, J=9.5 Hz, Ar-H).

2.   N,N-Dimethyl-2-[5-(2-methylimidazol-1-ylmethyl)-1H-indol-3-yl]ethylamine Trisoxalate Prepared from the preceding 4-nitrobenzyl imidazole using the general procedure described for Example 5. The trisoxalate salt was prepared, mp 160°–163° C. (MeOH/Et$_2$O); (Found: C, 50.57; H, 5.25; N, 10.60. C$_{17}$H$_{22}$N$_4$.2.8 (C$_2$H$_2$O$_4$) requires C, 50.79; H, 5.21; N, 10.48%); m/e 282 (M+); δ (360 MHz, D$_2$O) 2.65 (3H, s, Me); 2.92 (6H, s, NMe$_2$); 3.25 (2H, t, J=7.3 Hz, CH$_2$); 3.50 (2H, t, J=7.3 Hz, CH$_2$); 5.42 (2H, s, CH$_2$); 7.18

(1H, d, J=8.4 Hz, Ar-H); 7.31–7.40 (2H, m, Ar-H); 7.40 (1H, s, Ar-H); 7.56 (1H, d, J=8.4 Hz, Ar-H); 7.66 (1H, s, Ar-H).

EXAMPLE 15

N,N-Dimethyl-2-[5-imidazol-1-ylmethyl-1H-indol-3-yl]ethylamine Bisoxalate

Prepared from imidazole and 4-nitrobenzyl bromide using the procedure described for Example 5. The bisoxalate salt was prepared, 165°–166° C. (MeOH/Et$_2$O); (Found: C, 53.30; H, 5.34; N, 12.18. C$_{16}$H$_{20}$N$_4$.2.05 (C$_2$H$_2$O$_4$) requires C, 53.30; H, 5.36; N, 12.37%); δ (360 MHz, D$_2$O) 2.92 (6H, s, NMe$_2$); 3.24 (2H, t, J=7.7 Hz, CH$_2$); 3.48 (2H, t, J=7.7 Hz, CH$_2$); 5.50 (2H, s, CH$_2$); 7.27 (1H, dd, J=1.5 and 8.4 Hz, Ar-H); 7.37 (1H, s, Ar-H); 7.45 (1H, s, Ar-H); 7.49 (1H, s, Ar-H); 7.56 (1H, d, J=8.4 Hz, Ar-H); 7.75 (1H, s, Ar-H); 8.78 (1H, s, Ar-H).

EXAMPLE 16

N,N-Dimethyl-2-[5-(2-methylimidazol-1-yl)-1H-indol-3-yl]ethylamine Sesquioxalate 1. 1-(4-Nitrophenyl)-2-methylimidazole Sodium hydride (4.87 g, 122.0 mmol, 60% dispersion in oil) was added to a solution of 2-methylimidazole (10 g, 122.0 mmol) in DMF (100 ml) and stirred at room temperature for 0.25 h. 1-Fluoro-4-nitrobenzene (17.18 g, 122.0 mmol) was added to the reaction mixture and stirred at room temperature for 16 h. Water (150 ml) and ethyl acetate (250 ml) were added, the aqueous separated and extracted with ethyl acetate (3×150 ml). The combined extracts were washed with water (3×150 ml), dried (Na$_2$SO$_4$) and evaporated to give the desired product (11.5 g, 47%); δ (360 MHz, CDCl$_3$) 2.24 (3H, s, Me); 7.06 (1H, d, J=1.5 Hz, Ar-H); 7.10 (1H, d, J=1.5 Hz, Ar-H); 7.50 (2H, d, J=9.5 Hz, Ar-H); 8.38 (2H, d, J=9.5 Hz, Ar-H).

2. N,N-Dimethyl-2-[5-(2-methylimidazol-1-yl)-1H-indol-3-yl]ethylamine Sesquioxalate Prepared from the preceding 4-nitrophenyl imidazole using the procedure described for Example 5. The sesquioxalate salt was prepared, mp 185°–186° C. (iPA/MeOH); (Found: C, 56.17; H, 5.99; N, 13.46. C$_{16}$H$_{20}$N$_4$.1.55 (C$_2$H$_2$O$_4$). 0.1 EtOH requires C, 56.19; H, 5.79; N, 13.58%); δ (360 MHz, D$_2$O) 2.55 (3H, s, Me); 2.93 (6H, s, NMe$_2$); 3.26 (2H, t, J=7.4 Hz, CH$_2$); 3.51 (2H, t, J=7.4 Hz, CH$_2$); 7.30 (1H, dd, J=2.0 and 8.7 Hz, Ar-H); 7.48 (1H, d, J=2.1 Hz, Ar-H); 7.51–7.53 (2H, m, Ar-H); 7.70 (1H, d, J=8.7 Hz, Ar-H); 7.79 (1H, d, J=2.0 Hz, Ar-H).

EXAMPLE 17

N,N-Dimethyl-2-[5-(1,2,4-triazol-1ylmethyl)-1H-indol-3-yl]ethylamine. Succinate. Procedure B A solution of 1-(4-hydrazinophenyl)methyl-1,2,4-triazole dihydrochloride (2 g, 7.6 mmol, Example 5 step 3) and 4-N,N-dimethylaminobutanal dimethylacetal (1.8 g, 11.2 mmol) in 4% aqueous sulphuric acid (70 ml) was heated at reflux for 2 h. After the reaction mixture was cooled to room temperature, ethyl acetate (200 ml) was added and the aqueous basified with K$_2$CO$_3$. The aqueous was separated and extracted further with ethyl acetate (2×150 ml). The combined organics were dried (Na$_2$SO$_4$) and evaporated, and the residue chromatographed on silica gel eluting with CH$_2$Cl$_2$/EtOH/NH$_3$ (30:8:1) to give the title-triazole (610 mg, 30%). The succinate salt was prepared by addition of a solution of succinic acid (0.27 g, 2.3 mmol) in methanol (3 ml) to a solution of the triazole (0.61 g, 2.3 mmol) in methanol (5 ml). The solvent was removed under vacuum and the resultant product recrystallised from isopropylalcohol, mp 118°–120° C.; (Found: C, 58.76; H, 6.27; N, 17.79. C$_{15}$H$_{19}$N$_3$.C$_4$H$_6$O$_4$ requires C, 58.90; H, 6.50; N, 18.08%).

EXAMPLE 18

N,N-Dimethyl-2-[5-(1,2,4-triazol-1-ylmethyl)-1H-indol-3-yl]ethylamine. Benzoate

The benzoate salt of N,N-dimethyl-2-[5-(1,2,4-triazol-1-ylmethyl)-1H-indol-3-yl]ethylamine was prepared by addition of a solution of benzoic acid in diethyl ether to a solution of the free base in ethanol/diethyl ether (1:4). The precipitated salt was recrystallised from ethanol, mp 178°–180° C.; (Found: C, 67.28; H, 6.55; N, 17.66. C$_{15}$H$_{19}$N$_3$.C$_6$H$_5$CO$_2$H requires C, 67.50; H, 6.44; N, 17.89%); $^1$H NMR (360 MHz, D$_2$O) δ 2.92 (6H, s, NMe$_2$); 3.22 (2H, t, J=7.3 Hz, CH$_2$); 3.46 (2H, t, J=7.3 Hz, CH$_2$); 5.52 (2H, s, CH$_2$); 7.22 (1H, dd, J=1.6 and 8.4 Hz, Ar-H); 7.36 (1H, s, Ar-H); 7.44–7.58 (4H, m, Ar-H); 7.65 (1H, s, Ar-H); 7.87–7.91 (2H, m, Ar-H); 8.06 (1H, s, Ar-H); 8.54 (1H, s, Ar-H).

EXAMPLE 19

N,N-Dimethyl-2-[5-(2-ethyltetrazol-5-ylmethyl)-1H-indol-3-yl]ethylamine. Oxalate Prepared as described for Example 3, using ethyl iodide. The oxalate salt was prepared, mp 140°–142° C.; (Found: C, 55.71; H, 6.26; N, 21.35. C$_{16}$H$_{22}$N$_6$.C$_2$H$_2$O$_4$ requires C, 55.66; H, 6.23; N, 21.64%); $^1$H NMR (360 MHz, D$_2$O) δ 1.54 (3H, t, J=7.4 Hz, CH$_3$); 2.91 (6H, s, NMe$_2$); 3.21 (2H, t, J=7.4 Hz, CH$_2$); 3.47 (2H, t, J=7.4 Hz, CH$_2$); 4.34 (2H, s, CH$_2$); 4.64 (2H, q, J=7.4 Hz, CH$_2$CH$_3$); 7.17 (1H, dd, J=1.5 and 8.4 Hz, Ar-H); 7.33 (1H, s, Ar-H); 7.48 (1H, d, J=8.4 Hz, Ar-H); 7.59 (1H, s, Ar-H).

EXAMPLE 20

N,N-Dimethyl-2-[5-(1-ethyltetrazol-5-ylmethyl)-1H-indol-3-yl]ethylamine. Oxalate Prepared using the procedure described for Example 4, using ethyl iodide. The oxalate salt was prepared, mp 179° C. (MeOH/Et$_2$O); (Found: C, 55.59; H, 6.23; N, 21.49. C$_{16}$H$_{22}$N$_6$.C$_2$H$_2$O$_4$ requires C, 55.66; H, 6.23; N, 21.64%); $^1$H NMR (360 MHz, D$_2$O) δ 1.32 (3H, t, J=7.4 Hz, CH$_3$); 2.90 (6H, s, NMe$_2$); 3.21 (2H, t, J=7.4 Hz, CH$_2$); 3.46 (2H, t, J=7.4 Hz, CH$_2$); 4.38 (2H, q, J=7.4 Hz, CH$_2$); 4.47 (2H, s, CH$_2$); 7.14 (1H, dd, J=1.5 and 8.4 Hz, Ar-H); 7.35 (1H, s, Ar-H); 7.50 (1H, d, J=8.4 Hz, Ar-H); 7.53 (1H, s, Ar-H).

EXAMPLE 21

N,N-Dimethyl-2-[5-(1,2,4-triazol-1-yl)-1H-indol-3-yl]ethylamine. Bisoxalate

Prepared as described for Example 16 from 1,2,4-triazole sodium derivative and 1-fluoro-4-nitrobenzene. The bisoxalate salt was prepared, mp 210° C. (MeOH/Et$_2$O); (Found: C, 50.11; H, 4.78; N, 16.35. C$_{14}$H$_{17}$N$_5$.1.9 (C$_2$H$_2$O$_4$) requires C, 50.14; H, 4.92; N, 16.43%); $^1$H NMR (360 MHz, D$_2$O) δ 2.92 (6H, s, NMe$_2$); 3.25 (2H, t, J=7.4 Hz, CH$_2$); 3.50 (2H, t, J=7.4 Hz, CH$_2$); 7.44 (1H, s, Ar—H); 7.47 (1H, dd, J=2.0 and 8.7 Hz, Ar-H); 7.63 (1H, d, J=8.7 Hz, Ar-H); 7.88 (1H, d, J=2.0 Hz, Ar-H); 8.36 (1H, s, Ar-H); 9.05 (1H, s, Ar-H).

EXAMPLE 22

4-[5-(2-Methylimidazol-1-yl)-1H-indol-3-yl]-N-methylpiperidine. Bisoxalate sesquihydrate A solution of N-methyl-4-(formylmethyl)piperidine (0.25 g, 1.8 mmol) and 4-(2-methylimidazolyl)phenyl hydrazine hydrochloride (0.48 g, 2.1 mmol) in 4% $H_2SO_4$ (25 ml) was heated at reflux for 16 h. The mixture was cooled to room temperature, basified with $K_2CO_3$ solution and extracted with $CH_2Cl_2$ (3×75 ml). The combined extracts were dried ($Na_2SO_4$) and evaporated and the residue purified by chromatography on silica-gel eluting with $CH_2Cl_2$/EtOH/$NH_3$ (60:8:1) to give the title-compound (0.12 g). The bisoxalate sesquihydrate salt was prepared, mp 65°–70° C. (hygroscopic); (Found: C, 52.97; H, 5.51; N, 11.07. $C_{18}H_{22}N_4.2(C_2H_2O_4).1.5H_2O$ requires C, 52.69; H, 5.83; N, 11.17%); $^1$H NMR (360 MHz, $D_2O$) δ 1.96–2.08 (2H, m, $CH_2$); 2.31–2.40 (2H, m, $CH_2$); 2.56 (3H, s, $CH_3$); 2.95 (3H, s, $CH_3$); 3.20–3.27 (3H, m, CH and $CH_2$); 3.64–3.68 (2H, m, $CH_2$); 7.28 (1H, dd, J=2 and 8.7 Hz, Ar-H); 7.44 (1H, s, Ar-H); 7.48 (1H, d, J=2 Hz, Ar-H); 7.53 (1H, d, J=2 Hz, Ar-H); 7.69 (1H, d, J=8.7 Hz, Ar-H); 7.81 (1H, d, J=2 Hz, Ar-H).

EXAMPLE 23

4-[5-(1,2,4-Triazol-1-ylmethyl)-1H-indol-3-yl]-N-methylpiperidine. Oxalate

A solution of N-methyl-4-(formylmethyl)piperidine (0.1 g, 0.71 mmol) and 4-(1,2,4-triazolylmethyl)phenyl hydrazine dihydrochloride (0.185 g, 0.71 mmol) in 4% $H_2SO_4$ was heated at reflux for 2 h. The mixture was cooled to room temperature, basified with $K_2CO_3$ solution and extracted with $CH_2Cl_2$ (2×100 ml). The crude product was chromatographed on silica-gel eluting with $CH_2Cl_2$/EtOH/$NH_3$ (40:8:1) to give the title-compound (60 mg). The oxalate salt was prepared, mp 218°–220° C.; (Found: C, 58.61; H, 6.03; N, 17.94. $C_{17}H_{21}N_5.1.02$ ($C_2H_2O_4$) requires C, 58.96; H, 6.38; N, 17.56%); $^1$H NMR (360 MHz, $D_2O$) δ 1.88–2.02 (2H, m, $CH_2$); 2.20–2.34 (2H, m, $CH_2$); 2.92 (3H, s, $CH_3$); 3.10–3.24 (3H, m, CH and $CH_2$); 3.60–3.64 (2H, m, $CH_2$); 5.51 (2H, s, $CH_2$); 7.21 (1H, dd, J=1.5 and 8.4 Hz, Ar-H); 7.26 (1H, s, Ar-H); 7.51 (1H, d, J=8.4 Hz, Ar-H); 7.69 (1H, s, Ar-H); 8.05 (1H, s, Ar-H); 8.55 (1H, s, Ar-H).

EXAMPLE 24

1H-4-[5-(2-Methylimidazol-1-yl)-1H-indol-3-yl]-piperidine. Bisoxalate dihydrate 1. 4-[5-(2-Methylimidazol-1-yl)-1H-indol-3-yl]-N-benzylpiperidine Prepared from N-benzyl-4-(formylmethyl)piperidine using the procedure described for Example 22; $^1$H NMR (360 MHz, CDCl$_3$) δ 1.80–1.94 (2H, m, $CH_2$); 1.98–2.06 (2H, m, $CH_2$); 2.14–2.24 (2H, m, $CH_2$); 2.33 (3H, s, $CH_3$); 2.76–2.85 (1H, m, CH); 3.02–3.08 (2H, m, $CH_2$); 3.60 (2H, s, $CH_2$); 7.03–7.10 (4H, m, Ar-H); 7.26–7.38 (5H, m, Ar-H); 7.41 (1H, d, J=8.5 Hz, Ar-H); 7.52 (1H, d, J=1.8 Hz, Ar-H); 8.30 (1H, br s, NH).

2. 1H-4-[5-(2-Methylimidazol-1-yl)-1H-indol-3-yl]-piperidine. Bisoxalate dihydrate To a solution of ammonium formate (0.32 g, 5.07 mmol) and 4-[5-(2-methylimidazol-1-yl)-1H-indol-3-yl]-N-benzylpiperidine (0.4 g, 1.08 mmol), in methanol (40 ml) was added Pd/C (10%; 0.4 g) and the mixture stirred at 60° C. for 3h. The catalyst was removed by filtration through celite and the solvent removed under vacuum. The residue was taken up into $H_2O$ (30 ml), basified with $NH_3$ solution and extracted with ethyl acetate (3×100 ml). The combined extracts were dried ($Na_2SO_4$) and evaporated and the residue chromatographed through silica-gel eluting with $CH_2Cl_2$/MeOH/$NH_3$ (30:8:1) to give the desired piperidine (0.2 g). The bisoxalate dihydrate salt was prepared, mp 80° C. (hygroscopic); (Found: C, 50.53; H, 5.54; N, 10.87. $C_{17}H_{20}N_4.2(C_2H_2O_4).2.2H_2O$ requires C, 50.43; H, 5.72; N, 11.20%); $^1$H NMR (360 MHz, $D_2O$) δ 1.91–2.03 (2H, m, $CH_2$); 2.30–2.34 (2H, m, $CH_2$); 2.55 (3H, s, $CH_3$); 3.19–3.36 (3H, m, CH and $CH_2$); 3.55–3.62 (2H, m, $CH_2$); 7.28 (1H, dd, J=1.2 and 8.6 Hz, Ar-H); 7.44 (1H, s, Ar-H); 7.47 (1H, d, J=2.0 Hz, Ar-H); 7.52 (1H, d, J=2.0 Hz, Ar-H); 7.69 (1H, d, J=8.6 Hz, Ar-H); 7.82 (1H, d, J=1.2 Hz, Ar-H).

EXAMPLE 25

1H-4-[5-(1,2,4-Triazol-1-ylmethyl)-1H-indol-3-yl]-piperidine. Oxalate

Prepared from N-benzyl-4-(formylmethyl)piperidine and 4-(1,2,4-triazolylmethyl)phenyl hydrazine dihydrochloride using the procedures described for Examples 23 and 24. The oxalate salt was prepared, mp 272° C.; (Found: C, 58.27; H, 5.56; N, 18.79. $C_{16}H_{19}N_5.C_2H_2O_4$ requires C, 58.21; H, 5.70; N, 18.86%); $^1$H NMR (360 MHz, $D_2O$) δ 1.86–1.98 (2H, m, $CH_2$); 2.24–2.28 (2H, m, $CH_2$); 3.15–3.36 (3H, m, CH and $CH_2$); 3.52–3.56 (2H, m, $CH_2$); 5.51 (2H, s, $CH_2$); 7.21 (1H, dd, J=1.6 and 8.5 Hz, Ar-H); 7.27 (1H, s, Ar-H); 7.52 (1H, d, J=8.5 Hz, Ar-H); 7.70 (1H, d, J=1.6 Hz, Ar-H); 8.09 (1H, s, Ar-H); 8.60 (1H, s, Ar-H).

EXAMPLE 26

1H-3-[5-(2-Methylimidazol-1-yl)-1-H-indol-3-yl]-pyrrolidine. Bisoxalate 1. 3-[5-(2-Methylimidazol-1-yl)-1H-indol-3-yl]-N-benzylpyrrolidine Prepared from N-benzyl-3-(formylmethyl)pyrrolidine and 4-(2-methylimidazolyl)phenyl hydrazine hydrochloride as described for Example 22; $^1$H NMR (360MHz, CDCl$_3$) δ 1.98–2.06 (1H, m, CH of $CH_2$); 2.34 (3H, s, $CH_3$); 2.34–2.44 (2H, m, 2 of CH of $CH_2$); 2.71 (1H, t, J=7.4 Hz, CH of $CH_2$); 2.80 (1H, t, J=6.9 Hz, CH of $CH_2$); 3.05 (1H, t, J=8.7 Hz, CH of $CH_2$) 3.61–3.73 (1H, m, CH); 3.72 (2H, ABq, J=13 Hz, $CH_2$); 6.95–7.14 (4H, m, Ar-H); 7.22–7.41 (5H, m, Ar-H); 7.40 (1H, d, J=8.5 Hz, Ar-H); 7.66 (1H, s, Ar-H); 8.30 (1H, br s NH).

2. 1H-3-[5-(2-Methylimidazol-1-yl)-1H-indol-3-yl]-pyrrolidine. Bisoxalate

Prepared from the preceding N-benzylpyrrolidine using the procedure described for Example 24. The bisoxalate salt was prepared, mp 210°–213° C. (methanol/ether); (Found: C, 53.93; H, 5.22; N, 12.50. $C_{16}H_{18}N_4.2(C_2H_2O_4)$ requires C, 53.81; H, 4.97; N, 12.55%); $^1$H NMR (360 MHz, $D_2O$) δ 2.91–2.30 (1H, m, CH of $CH_2$); 2.55 (3H, s, $CH_3$); 2.55–2.60 (1H, m, CH of $CH_2$); 3.35–3.64 (3H, m, CH and $CH_2$); 3.80–3.90 (2H, m, $CH_2$); 7.30 (1H, dd, J=2 and 8.6 Hz, Ar-H); 7.47 (1H, d, J-2 Hz, Ar-H); 7.50 (1H, s, Ar-H); (7.53 (1H, d, J=2 Hz, Ar-H); 7.70 (1H, d, J=8.6 Hz, Ar-H); 7.80 (1H, d, J=2 Hz, Ar-H).

EXAMPLE 27

N-Methyl-3-[5-(2-methylimidazol-1-yl)-1H-indol-3-yl]-pyrrolidine. Bisoxalate

To a cooled (0° C.), stirred mixture of 1H-3-[5-(2-methylimidazol-1-yl)-1H-indol-3-yl]pyrrolidine (0.12 g, 0.45 mmol), acetic acid (0.136 g, 2.3 mmol) and NaCNBH$_3$ (71 mg, 1.1 mmol), in methanol (15 ml), was added dropwise a solution of formaldehyde (89 mg of a 38% w/w solution in H$_2$O, 1.1 mmol) in methanol (10 ml). The mixture was stirred at 0° C. for 0.1 h before warming to room temperature and stirring for 1.5 h. Saturated K$_2$CO$_3$ solution (10 ml) was added and the solvent removed under vacuum. The residue was extracted with ethyl acetate (3×100 ml) and the combined extracts dried (Na$_2$SO$_4$) and evaporated. The crude product was chromatographed on silica-gel eluting with CH$_2$Cl$_2$/MeOH/NH$_3$ (60:8:1) to give the title product (0.1 g). The bisoxalate salt was prepared, mp 191°–194° C. (MeOH/Et$_2$O); (Found: C, 54.39; H, 5.30; N, 11.87. C$_{17}$H$_{20}$N$_4$.2(C$_2$H$_2$O$_4$).0.2H$_2$O requires C, 54.36; H, 5.30; N, 12.07%); $^1$H NMR (360 MHz, D$_2$O) δ 2.26–2.45 (1H, m, CH of CH$_2$); 2.55 (3H, s, Me); 2.62–2.75 (1H, m, CH of CH$_2$); 3.02 and 3.03 (total 3H, s, Me); 3.23–3.45 (2H, m, CH$_2$); 3.60–3.68, 3.77–4.1 and 4.12–4.15 (total 3H, each m, CH and CH$_2$); 7.30 (1H, d, J=8.9 Hz, Ar—H); 7.48 (1H, d, J=2.2 Hz, Ar—H); 7.52 (1H, s, Ar—H); 7.53 (1H, d, J=2.2 Hz, Ar—H); 7.70 (1H, d, J=8.9 Hz, Ar—H); 7.78 (1H, s, Ar—H).

EXAMPLE 28

1H-4-[5-Imidazol-1-yl-1H-indol-3-yl]piperidine. Bisoxalate

Prepared from N-benzyl-4-(formylmethyl)piperidine and 4-(imidazolyl)phenyl hydrazine hydrochloride using the procedures described for Examples 22 and 24. The bisoxalate salt was prepared, mp 155°–157° C.; (Found: C, 54.32; H, 5.50; N, 11.66. C$_{16}$H$_{18}$N$_4$.2(C$_2$H$_2$O$_4$).0.3(Et$_2$O) requires C, 54.33; H, 5.38; N, 11.96%); $^1$H NMR (360 MHz, D$_2$O) δ 1.90–2.04 (2H, m, CH$_2$); 2.32 (2H, br d, J=13 Hz, CH$_2$); 3.20–3.32 (3H, m, CH and CH$_2$); 3.55–3.60 (2H, m, CH$_2$); 7.41–7.44 (2H, m, Ar—H); 7.64 (1H, s, Ar—H); 7.68 (1H, d, J=8.7 Hz, Ar—H); 7.85 (1H, s, Ar—H); 7.92 (1H, d, J=2 Hz, Ar—H); 9.06 (1H, s, Ar—H).

EXAMPLE 29

1H-4-[5-(1,2,3-Triazol-1-yl)-1H-indol-3-yl]piperidine. Hemioxalate

Prepared from N-benzyl-4-(formylmethyl)piperidine and 4-(1,2,3-triazolyl)phenyl hydrazine hydrochloride using the procedures described for Examples 22 and 24. The hemioxalate salt was prepared, mp 278° C. (MeOH/Et$_2$O); (Found: C, 61.84; H, 6.10; N, 22.21. C$_{15}$H$_{17}$N$_5$.0.5(C$_2$H$_2$O$_4$) requires C, 61.53; H, 5.81; N, 22.42%); $^1$H NMR (360 MHz, D$_6$-DMSO) δ 1.66–1.82 (2H, m, CH$_2$); 1.98–2.06 (2H, m, CH$_2$); 2.83–2.89 (2H, m, CH$_2$); 2.98–3.08 (1H, m, CH); 3.21 (2H, br d, J=12.5 Hz, CH$_2$); 7.28 (1H, s, Ar—H); 7.51–7.56 (2H, m, Ar—H); 7.93 (1H, s, Ar—H); 8.05 (1H, s, Ar—H); 8.73 (1H, s, Ar—H).

EXAMPLE 30

N-Methyl-4-[5-imidazol-1-yl-1H-indol-3-yl]piperidine. Sesquioxalate

Prepared from N-methyl-4-(formylmethyl)piperidine and 4-(imidazolyl)phenyl hydrazine hydrochloride as described for Example 22. The sesquioxalate salt was prepared, mp 217° C.; (Found: C, 57.41; H, 5.83; N, 13.30. C$_{17}$H$_{20}$N$_4$. 1.5(C$_2$H$_2$O$_4$).0.14(CH$_3$OH) requires C, 57.61; H, 5.66; N, 13.34%); $^1$H NMR (360 Mhz, D$_2$O) δ 1.94–2.06 (2H, m, CH$_2$); 2.34–2.38 (2H, m, CH$_2$); 2.94 (3H, s, CH$_3$); 3.20–3.27 (3H, m, CH and CH$_2$); 3.63–3.67 (2H, m, CH$_2$); 7.40–7.43 (2H, m, Ar—H); 7.64 (1H, s, Ar—H); 7.68 (1H, d, J=8.7 Hz, Ar—H); 7.84 (1H, s, Ar—H); 7.90 (1H, d, J=1.3 Hz, Ar—H); 9.07 (1H, s, Ar—H).

EXAMPLE 31

N-Methyl-4-[5-(1,2,3-triazol-1-yl)-1H-indol-3-yl]piperidine. Hemioxalate

Prepared from N-methyl-4-(formylmethyl)piperidine and 4-(1,2,3-triazolyl)phenyl hydrazine hydrochloride as described for Example 22. The hemioxalate salt was prepared, mp 251°–254° C. (MeOH/Et$_2$O); (Found: C, 62.21; H, 6.49; N, 21.21. C$_{16}$H$_{19}$N$_5$.0.5(C$_2$H$_2$O$_4$).0.1H$_2$O requires C, 62.22; H, 6.20; N, 21.34%); $^1$H NMR (360 MHz, D$_2$O) δ 1.69–2.01 (2H, m, CH$_2$); 2.25–2.31(2H, m, CH$_2$); 2.94 (3H, s, CH$_3$); 3.04–3.20 (3H, m, CH and CH$_2$); 3.61–3.65 (2H, m, CH$_2$); 7.32 (1H, s, Ar-H); 7.44 (1H, dd, J=1.9 and 8.7 Hz, Ar-H); 7.58 (1H, d, J=8.7 Hz, Ar-H); 7.86 (1H, d, J=1.8 Hz, Ar-H); 7.94 (1H, s, Ar-H); 8.29 (1H, s, Ar-H).

EXAMPLE 32

N-Methyl-3-[5-(1,2,3-triazol-1-yl)-1H-indol-3-yl]pyrrolidine. Oxalate

Prepared from N-benzyl-3-(formylmethyl)pyrrolidine and 4-(1,2,3-triazolyl)phenyl hydrazine hydrochloride as described for Examples 26 and 27. The oxalate salt was prepared, mp 154°–156° C. (MeOH/Et$_2$O); (Found: C, 57.06; H, 5.39; N, 19.43. C$_{15}$H$_{17}$N$_5$.C$_2$H$_2$O$_4$ requires C, 57.14; H, 5.36; N, 19.60%); $^1$H NMR (360 MHz, D$_2$O) δ 2.23–2.38 (1H, m, CH of CH$_2$); 2.55–2.69 (1H, m, CH of CH$_2$); 3.01 (3H, s, Me); 3.13–3.42 and 3.55–3.60 (total 2H, each m, CH$_2$); 3.70–4.09 (3H, m, CH and CH$_2$); 7.39 (1H, d, J=8.7 Hz, Ar-H); 7.42–7.46 (1H, m, Ar-H); 7.58 (1H, d, J=8.7 Hz, Ar-H); 7.62 (1H, s, Ar-H); 7.93 (1H, s, Ar-H); 8.30 (1H, s, Ar-H).

EXAMPLE 33

N-Methyl-3-[5-(2-methylimidazol-1-ylmethyl)-1H-indol-3-yl]pyrrolidine. Bisoxalate Prepared from N-benzyl-3-(formylmethyl)pyrrolidine and 4-(2-(methyl)imidazol-1-ylmethyl)phenyl hydrazine hydrochloride as described for Examples 26 and 27. The bisoxalate salt was prepared, mp 152°–153° C.; (Found: C, 55.41; H, 5.51; N, 11.61. C$_{18}$H$_{22}$N$_4$.2(C$_2$H$_2$O$_4$) requires C, 55.69; H, 5.52; N, 11.81%); $^1$H NMR (360 MHz, D$_2$O) δ 2.22–2.46 (1H, m, CH of CH$_2$); 2.58–2.76 (1H, m, CH of CH$_2$); 2.65 (3H, s, Me); 3.02 and 3.03 (total 3H, s, Me); 3.21–3.44, 3.60–3.67, 3.75–3.95 and 4.09–4.14 (total 5H, each m, CH and 2 of CH$_2$); 5.42 (2H, s, CH$_2$); 7.17–7.19 (1H, m, Ar-H); 7.32 (2H, s, Ar-H); 7.39 (1H, d, J=8.4 Hz, Ar-H); 7.56 (1H, d, J=8.4 Hz, Ar-H); 7.67 (1H, s, Ar-H).

EXAMPLE 34

N-Methyl-3-[5-imidazol-1yl-1H-indol-3-yl]pyrrolidine. Bisoxalate

Prepared from N-benzyl-3-(formylmethyl)pyrrolidine and 4-(imidazolyl)phenyl hydrazine hydrochloride using the procedures described for Examples 26 and 27. The bisoxalate salt was prepared, mp 173°–175° C. (MeOH/Et$_2$O); (Found: C, 53.94; H, 5.07; N, 12.51.C$_{16}$H$_{18}$N$_4$.2(C$_2$H$_2$O$_4$) requires C, 53.81; H, 4.97; N, 12.55%); $^1$H NMR (360 MHz, D$_2$O) δ 2.26–2.45 and 2.60–2.78 (each 1H, each m, CH$_2$), 3.03 (total 3H, each s, Me), 3.23–3.45, 3.61–3.66, 3.78–3.95 and 4.11–4.16 (total 5H, each m, 2 of CH$_2$ and CH), 7.42 and 7.45 (total 1H, each s, Ar-H), 7.49 (1H, d, J=9.2 Hz, Ar-H), 7.65 (1H, s, Ar-H), 7.69 (1H, d, J=9.2 Hz, Ar-H), 7.86–7.89 (2H, m, Ar-H), 9.09 (1H, s, Ar-H).

EXAMPLE 35

N-Methyl-3-[5-(1,2,4-triazol-1-ylmethyl)-1H-indol-3-yl]pyrrolidine. Sesquioxalate. Hemihydrate Prepared from N-benzyl-3-(formylmethyl)pyrrolidine and 4-(1,2,4-triazolylmethyl)phenyl hydrazine dihydrochloride as described for Examples 26 and 27. The sesquioxalate hemihydrate salt was prepared, mp 59°–61° C. (isopropyl alcohol/Et$_2$O); (Found: C, 55.10; H, 5.79; N, 16.99. C$_{16}$H$_{19}$N$_5$.1.3(C$_2$H$_2$O$_4$).0.4H$_2$O requires C, 55.08; H, 5.57; N, 17.27%); $^1$H NMR (360 MHz, D$_2$O) δ 2.20–2.42 and 2.54–2.72 (each 1H, each m, CH$_2$), 3.00 and 3.02 (total 3H, each s, Me), 3.16–3.42, 3.56–3.62, 3.72–3.76, 3.82–3.94 and 3.98–4.10 (total 5H, each m, 2 of CH$_2$ and CH), 5.52 (2H, s, CH$_2$), 7.22 and 7.24 (total 1H, each s, Ar-H), 7.34 (1H, d, J=8.6 Hz, Ar-H), 7.52 (1H, d, J=8.6 Hz, Ar-H), 7.66 (1H, s, Ar-H), 8.06 (1H, s, Ar-H), 8.58 (1H, s, Ar-H).

EXAMPLE 36

N-Methyl-3-[5-imidazol-1-ylmethyl-1H-indol-3-yl]pyrrolidine. Oxalate. Hemihydrate Prepared from N-benzyl-3-(formylmethyl)pyrrolidine and 4-(imidazol-1-ylmethyl)phenyl hydrazine hydrochloride as described for Examples 26 and 27. The oxalate hemihydrate salt was prepared, mp 101°–104° C. (isopropyl alcohol/Et$_2$O); (Found: C, 59.51; H, 6.35; N, 14.54. C$_{17}$H$_{20}$N$_4$.C$_2$H$_2$O$_4$.0.6H$_2$O.0.1 ($^i$PrOH) requires C, 59.86; H, 6.25; N, 14.47%); $^1$H NMR (360 MHz, D$_2$O) δ 2.26–2.42 (1H, m, CH of CH$_2$), 2.60–2.74 (1H, m, CH of CH$_2$), 3.03 (3H, s, Me), 3.16–4.12 (5H, br m, 2 of CH$_2$ and CH), 5.45 (3H, s, Me), 7.27 (1H, dd, J=1.6 and 8.5 Hz, Ar-H), 7.31 (1H, s, Ar-H), 7.38–7.40 (2H, m, Ar-H), 7.58 (1H, d, J=8.5 Hz, Ar-H), 7.70 (1H, s, Ar-H), 8.39 (1H, s, Ar-H).

EXAMPLE 37

N,N-Dimethyl-2-[5-(2-aminoimidazol-1-yl)-1H-indol-3-yl]ethylamine. Bisoxalate

Prepared from 2-aminoimidazole and 4-fluoro nitrobenzene as described for Example 16. To prevent reaction of the aminoimidazole with sodium nitrite under the diazotization conditions the amino was protected as the acetamide with Ac$_2$O/AcOH prior to hydrogenation and hydrazine formation. Fischer reaction of 4-[2-(methylcarbonylamino)imidazol-1-yl]phenyl hydrazine with N,N-dimethylaminobutanal dimethylacetal gave the title-product. The bisoxalate salt was prepared, mp 199°–200° C. (MeOH/Et$_2$O); (Found: C, 50.35; H, 5.06; N, 15.05. C$_{15}$H$_{19}$N$_5$.2.1(C$_2$H$_2$O$_4$) requires C, 50.31; H, 5.10; N, 15.28%); $^1$H NMR (360 MHz, D$_2$O) δ 2.91 (6H, s, N(Me)$_2$), 3.27 (2H, t, J=7.4 Hz, CH$_2$), 3.50 (2H, t, J=7.4 Hz, CH$_2$), 6.97 (2H, s, Ar-H), 7.29 (1H, dd, J=1.8 and 8.7 Hz, Ar-H), 7.48 (1H, s, Ar-H), 7.67 (1H, d, J=8.7 Hz, Ar-H), 7.78 (1H, d, J=1.8 Hz, Ar-H).

EXAMPLE 38

N,N-Dimethyl-2-[5-(2-aminoimidazol-1-ylmethyl)-1H-indol-3-yl]ethylamine. Sesquioxalate 1. 4-Cyanophenylhydrazine. Hydrochloride To a cooled (−15° C.) and stirred suspension of 4-aminobenzonitrile (50 g, 423 mmol) in concentrated hydrochloric acid (550 ml) was added dropwise a solution of sodium nitrite (31.5 g, 457 mmol) in water (200 ml) at such a rate as to maintain the temperature below −10° C. After the addition was finished, the reaction mixture was quickly filtered to remove solids and the filtrate was added portionwise to a cooled (−20° C.) and stirred solution of tin (II) chloride dihydrate (477 g, 2.1 mol) in concentrated hydrochloric acid (370 ml) at such a rate as to maintain the temperature below −10° C. After further 15 minutes at −10° to 0° C., the white precipitate was collected by filtration, washed with diethyl ether (4×250 ml) and dried to give 56 g (78%) of the title compound; mp 235°–237° C. (ethanolwater 1:1); $^1$H NMR (250 MHz, DMSO-d$_6$) δ 10.50 (3H, br s, —N$^+$H$_3$), 9.10 (1H, br s, —NH—), 7.71 (2H, d, J=8.8 Hz, Ar-H), 7.03 (2H, d, J=8.8 Hz, Ar-H); m/z (CI) 132 (M$^+$−1).

2. 2-[5-Cyano-1H-indol-3-yl]ethylamine. Hydrochloride

To a stirred suspension of 4-cyanophenylhydrazine (50 g) in a mixture of ethanol and water (5:1; 21) was added 4-chlorobutanal dimethylacetal (45 g) and the resulting mixture was refluxed for 18 hours. Solvents were removed under vacuum and the residue was azeotroped with toluene to give a brown solid. Crystallisation of this crude material from methanol (150 ml) gave 23 g (35%) of the title compound as a yellow solid; mp 270°–274° C.; $^1$H NMR (250 MHz, DMSO-d$_6$) δ 11.60 (1H, br s, indole N-H), 8.17 (1H, d, J=1.1 Hz, Ar-H), 7.97 (3H, br s, —N$^+$H$_3$), 7.54 (1H, d, J=8.5 Hz, Ar-H), 7.46 (1H, s, Ar-H), 7.44 (1H, dd, J=8.5 and 1.1 Hz, Ar-H), 3.05 (4H, br s, —CH$_2$CH$_2$N—); m/z (CI) 184 (M$^+$−1).

3. N-tert-Butyloxycarbonyl-2-[5-cyano-1H-indol-3-yl]ethylamine.

The title compound was prepared in 58% yield from the preceding tryptamine using the conditions described for Example 1 (Step 4); white solid; mp 132°–134° C. (hexane-ethyl acetate); $^1$H NMR (250 MHz, CDCl$_3$) δ 8.42 (1H, br s, indole N—H), 7.93 (1H, s, Ar-H), 7.41 (2H, s, Ar-H), 7.12 (1H, d, J=2.2 Hz, Ar-H), 4.71 (1H, br s, —NH—), 3.44 (2H, q, J=6.9 Hz, —CH$_2$NH—), 2.94 (2H, t, J=6.9 Hz, Ar-CH$_2$—), 1.45 (9H, s, t-Bu); m/z (CI) 286 (M$^+$+1).

4. N-tert-Butyloxycarbonyl-2-[5-aminomethyl-1H-indol-3-yl]ethylamine.

A solution of the product from the previous step (11.3 g) in a mixture of absolute ethanol (750 ml) and chloroform (22 ml) was hydrogenated at 50 psi over platinum (IV) oxide (1 g) for 28 hours. The catalyst was removed by filtration and solvents were removed under vacuum. Flash chromatography of the residue (silica gel, dichloromethane-methanol-ammonia 90:10:1) gave 9.5 g (82%) of the title compound as a white solid; mp 147°–149° C.; $^1$H NMR (360 MHz, CDCl$_3$) δ 8.04 (1H, br s, indole N—H), 7.52 (1H, s, Ar-H), 7.33 (1H, d, J=8.4 Hz, Ar-H), 7.16 (1H, d, J=8.4 Hz, Ar-H), 7.03 (1H, s, Ar-H), 4.61 (1H, br s, —NHBOC), 3.96 (2H, s, Ar-CH$_2$NH$_2$), 3.45 (2H, br q, —CH$_2$NHBOC), 2.95 (2H, t, J=6.8 Hz, Ar-CH$_2$—), 1.43 (9H, s, t-Bu); m/z (CI) 288 (M+ −1).

5. N-tert-Butyloxycarbonyl-2-[5-dimethylaminomethyl-1H-indol-3-yl]ethylamine.

The title compound was prepared in 71% yield from the product from the previous step using the conditions described for Example 3 (Step 3); colourless thick oil; $^1$H NMR (250 MHz, CDCl$_3$) δ 8.07 (1H, br s, indole N-H), 7.50 (1H, s, Ar-H), 7.31 (1H, d, J=8.3 Hz, Ar-H), 7.16 (1H, d, J=8.3 Hz, Ar-H), 7.02 (1H, s, Ar-H), 4.61 (1H, br s, —NH—), 3.54 (2H, s, Ar—CH$_2$N—), 3.45 (2H, q, J=6.2 Hz, —CH$_2$NH—), 2.94 (2H, t, J=6.2 Hz, Ar-CH$_2$—), 2.27 (6H, s, —NMe$_2$), 1.43 (9H, s, t-Bu).

6. N-tert-Butyloxycarbonyl-2-[5-trimethylammoniummethyl-1H-indol-3-yl]ethylamine. Iodide A solution of the product from step 5 (2.9 g) in a mixture of anhydrous diethyl ether (170 ml) and iodomethane (36 ml) was allowed to stand at room temperature for 16 hours in the dark. The white solid was collected by filtration, washed with diethyl ether and dried over phosphorous pentoxide at 50° C. under vacuum to give 4.2 g (100%) of the title compound; mp 199°–202° C. (decomposition); $^1$H NMR (360 MHz, DMSO-d$_6$) δ 11.09 (1H, br s, indole N—H), 7.69 (1H, s, Ar-H), 7.44 (1H, d, J=8.3 Hz, Ar-H), 7.26 (1H, s, Ar-H), 7.19 (1H, d, J=8.3 Hz, Ar-H), 6.89 (1H, br t, —NH—), 4.57 (2H, s, Ar-CH$_2$N—), 3.23 (2H, q, J=7.6 Hz, —CH$_2$NH—), 3.01 (9H, s, —N$^+$Me$_3$), 2.83 (2H, t, J=7.6 Hz, Ar-CH$_2$—), 1.37 (9H, s, t-Bu); m/z (FAB) 332. (Found: C, 49.30; H, 6.55; N, 9.79. C$_{19}$H$_{30}$IN$_3$O$_2$ requires: C, 49.68; H, 6.58; N, 9.15%).

7. N-tert-Butyloxycarbonyl-2-[5-(2-nitroimidazol-1-ylmethyl)-1H-indol-3-yl]ethylamine.

Sodium hydride (0.6 g of a 60% dispersion in oil) was added to a stirred solution of 2-nitroimidazole (1.61 g, 14.2 mmol) in DMF (65 ml), at room temperature. After 0.5 h, a solution of the preceding methiodide (3.26 g, 7.1 mmol) in DMF (40 ml) was added and the mixture refluxed for 2 h and then stirred at room temperature for 18 h. Aqueous work-up followed by flash chromatography of the crude product, afforded the title-compound (2.6 g); $^1$H NMR (360 MHz, CDCl$_3$) δ 1.43 (9H, s, t-Bu), 2.94 (2H, t, J=7.0 Hz, CH$_2$), 3.40–3.48 (2H, m, CH$_2$), 5.69 (2H, s, CH$_2$), 7.01 (1H, s, Ar-H), 7.09 (1H, d, J=8.4 Hz, Ar-H), 7.10 (2H, s, Ar-H), 7.37 (1H, d, J=8.4 Hz, Ar-H), 7.54 (1H, s, Ar-H), 8.12 (1H, s, indole-NH).

8. 2-[5-(2-Nitroimidazol-1-ylmethyl)-1H-indol-3-yl]ethylamine.

A solution of the preceding imidazole (2.6 g, 6.7 mmol) in 90% HCO$_2$H (150 ml) was stirred at room temperature for 1.25 h. The reaction was quenched by addition of MeOH and the solvents removed under vacuum. The crude product was purified by flash chromatography on silica-gel eluting with CH$_2$Cl$_2$/EtOH/NH$_3$ (30:8:1). The product (0.73 g) was obtained as a yellow oil; $^1$H NMR (360 MHz, d$_4$-MeOH) δ 2.87–2.94 (4H, m, 2 of CH$_2$), 5.71 (2H, s, CH$_2$), 7.05 (1H, d, J=8.4 Hz, Ar-H), 7.11 (1H, s, Ar-H), 7.12 (1H, s, Ar-H), 7.35 (1H, d, J=8.4 Hz, Ar-H), 7.39 (1H, s, Ar-H), 7.55 (1H, s, Ar-H).

9. N,N-Dimethyl-2-[5-(2-nitroimidazol-1-ylmethyl)-1H-indol-3-yl]ethylamine.

Prepared from the preceding tryptamine using the conditions described for Example 3 (Step 3); $^1$H NMR (250 MHz, CDCl$_3$) δ 2.33 (6H, s, N(Me)$_2$), 2.62 (2H, t, J=7.4 Hz, CH$_2$), 2.92 (2H, t, J=7.4 Hz, CH$_2$), 5.68 (2H, s, CH$_2$), 7.00 (1H, d, J=1.0 Hz, Ar-H), 7.07 (1H, dd, J=1.0 and 8.2 Hz, Ar-H), 7.09 (1H, d, J=2.4 Hz, Ar-H), 7.10 (1H, d, J=2.4 Hz, Ar-H), 7.35 (1H, d, J=8.2 Hz, Ar-H), 7.53 (1H, s, Ar-H), 8.19 (1H, br s, indole-NH).

10. N,N-Dimethyl-2-[5-(2-aminoimidazol-1ylmethyl)-1H-indol-3-yl]ethylamine. Sesquioxalate The title-compound was prepared from the product of Step 9 using the conditions described for Example 5 (Step 2). The sesquioxalate salt was prepared, mp 211°–212° C. (MeOH/Et$_2$O); (Found: C, 54.46; H, 6.08; N, 16.53. C$_{16}$H$_{21}$N$_5$.1.5(C$_2$H$_2$O$_4$).0.06 (MeOH) requires C, 54.46; H, 5.81; N, 16.66%); $^1$H NMR (360 MHz, D$_2$O) δ 2.91 (6H, s, N(Me)$_2$), 3.25 (2H, t, J=7.4 Hz, CH$_2$), 3.49 (2H, t, J=7.4 Hz, CH$_2$), 5.16 (2H, s, CH$_2$), 6.77 (1H, d, J=2.3 Hz, Ar-H), 6.83 (1H, d, J=2.3 Hz, Ar-H), 7.19 (1H, dd, J=1.5 and 8.5 Hz, Ar-H), 7.39 (1H, s, Ar-H), 7.56 (1H, d, J=8.5 Hz, Ar-H), 7.61 (1H, s, Ar-H).

EXAMPLE 39

N-Methyl-2-[5-(1,2,4-triazol-1-ylmethyl)-1H-indol-3-yl]ethylamine. Oxalate.

1. N-Benzyl-2[5-(1,2,4-triazol-1-ylmethyl)-1H-indol-3-yl]ethylamine.

To a solution of 2-[5-(1,2,4-triazol-1-ylmethyl)-1H-indol-3-yl]ethylamine (1.5 g, 6.2 mmol) in EtOH (30 ml) was added freshly distilled benzaldehyde (0.66 g, 6.2 mmol) and the solution stirred at room temperature for 21 h. NaBH$_4$ (0.24 g, 6.3 mmol) was added portionwise over 10 min, at room temperature, and the resulting mixture was stirred for 0.5 h before the solvent was removed under vacuum. The resulting residue was taken up into water (10 ml) and acidified with 1N HCl (15 ml). The mixture was then basified with 2N NaOH and extracted with EtOAc (4×50 ml). The combined organic phases were washed with brine (30 ml), dried and concentrated. Chromatography of the residue on silica-gel eluting with CH$_2$Cl$_2$/MeOH (85:15) gave the title-product (1.38 g, 67%); $^1$H NMR (360 MHz, CDCl$_3$) δ 2.94 (4H, s, 2 of CH$_2$), 3.80 (2H, s, CH$_2$), 5.38 (2H, s, CH$_2$), 7.04 (1H, d, J=2 Hz, Ar-H), 7.08 (1H, dd, J=1.5 and 8.4 Hz, Ar-H), 7.18–7.30 (5H, m, Ar-H), 7.32 (1H, d, J=8.4 Hz, Ar-H), 7.54 (1H, s, Ar-H), 7.94 (1H, d, J=2 Hz, Ar-H), 8.17 (1H, br s, indole-NH).

2. N-Benzyl-N-methyl-2-[5-(1,2,4-triazol-1-ylmethyl)-1H-indol-3-yl]ethylamine.

To a stirred solution of the preceding amine (1.14 g, 3.4 mmol) in anhydrous DMF (45 ml) was added K$_2$CO$_3$ (0.89 g, 6.4 mmol) and dimethyl sulphate (0.46 g, 3.7 mmol). The mixture was stirred at room temperature for 3.5 h before adding H$_2$O (90 ml) and extracting with EtOAc (2×100 ml). The combined organic solutions were washed with brine (40 ml), dried, and concentrated. The residue was chromatographed on silica-gel eluting with CH$_2$Cl$_2$/MeOH (90:10) to give the desired product (0.69 g); $^1$H NMR (360 MHz, CDCl$_3$) δ 2.34 (3H, s, CH$_3$), 2.70–2.76 (2H, m, CH$_2$), 2.94–3.00 (2H, m, CH$_2$), 3.60 (2H, s, CH$_2$), 5.38 (2H, s, CH$_2$), 7.04 (1H, d, J=2 Hz, Ar-H), 7.08 (1H, dd, J=2 and 8.4 Hz, Ar-H), 7.20–7.36 (6H, m, Ar-H), 7.44 (1H, s, Ar-H), 7.94 (1H, s, Ar-H), 7.96 (1H, s, Ar-H), 8.18 (1H, br s, indole-NH).

3. N-Methyl-2-[5-(1,2,4-triazol-1-ylmethyl)-1H-indol-3-yl]ethylamine. Oxalate.

A solution of the preceding benzylamine (0.69 g, 2.0 mmol) in ethanol (100 ml) and 2N HCl (2 ml) was hydrogenated at 30 psi over 10% Pd/C (0.6 g) for 4 h. The catalyst was removed by filtration through hyflo, the solvent removed under vacuum, and the residue chromatographed on silica-gel eluting with $CH_2Cl_2/EtOH/NH_3$ (40:8:1) to give the title-N-methylamine (0.34 g, 68%). The oxalate salt was prepared and recrystallised from isopropyl alcohol; mp 149°–150° C.; (Found: C, 55.42; H, 5.72; N, 19.55. $C_{14}H_{17}N_5.C_2H_2O_4$. 0.15 (iPA) requires C, 55.72; H, 5.75; N, 19.76%); $^1$H NMR (360 MHz, $D_2O$) δ 2.44 (3H, s, $CH_3$), 2.87–2.98 (4H, m, 2 of $CH_2$), 5.41 (2H, s, $CH_2$), 7.05 (1H, s, Ar-H), 7.09 (1H, dd, J=1.6 and 8.4 Hz, Ar-H), 7.31 (1H, d, J=8.4 Hz, Ar-H), 7.57 (1H, s, Ar-H), 7.96 (1H, s, Ar-H), 7.99 (1H, s, Ar-H).

EXAMPLE 40

Tablet Preparation

Tablets containing 1.0, 2.0, 25.0, 26.0, 50.0 and 100.0 mg, respectively of the following compounds are prepared as illustrated below:

N,N-Dimethyl-2-[5-(2-methyltetrazol-5-ylmethyl)-1H-indol-3-yl]ethylamine. Oxalate.

N,N-Dimethyl-2-[5-(1,2,4-triazol-1-ylmethyl)-1H-indol-3-yl]ethylamine. Benzoate.

N,N-Dimethyl-2-[5-(1,2,3,4-tetrazol-1-ylmethyl)-1H-indol-3-yl]ethylamine. Succinate.

N-Methyl-4-[5-imidazol-1-yl-1H-indol-3-yl]piperidine. Sesquioxalate.

N-Methyl-3-[5-(1,2,3-triazol-1-yl)-1H-indol-3-yl]pyrrolidine. Oxalate.

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:

1. The compound which is N,N-dimethyl-2-[5-(1,2,4-triazol-1-ylmethyl)-1H-indol-3-yl]ethylamine, or a pharmaceutically acceptable salt thereof.

2. A salt of the compound according to claim 1 selected from the group consisting of the oxalate, succinate, benzoate and hydrochloride salts.

3. A pharmaceutical composition comprising a therapeutically effective amount of N,N-dimethyl-2-[5-(1,2,4-triazol-1-ylmethyl)-1H-indol-3-yl]ethylamine or a pharmaceutically acceptable salt thereof in association with a pharmaceutically acceptable carrier or excipient.

4. A pharmaceutical composition according to claim 3 wherein the pharmaceutically acceptable salt is selected from the group consisting of the oxalate, succinate, benzoate and hydrochloride salts.

5. A method for the treatment of migraine, cluster headache, chronic paroxysmal hemicrania, headache associated with vascular disorders, tension headache and pediatric migraine, which comprises administering to a patient in need of such treatment an effective amount of N,N-dimethyl-2-[5-(1,2,4-triazol-1-ylmethyl)-1H-indol-3-yl]ethyl amine or a pharmaceutically acceptable salt thereof.

6. A method according to claim 5 wherein the pharmaceutically acceptable salt is selected from the group consisting of the oxalate, succinate, benzoate and hydrochloride salts.

* * * * *

UNITED STATES PATENT AND TRADEMARK OFFICE
CERTIFICATE OF CORRECTION

PATENT NO. : 5,298,520

DATED : March 29, 1994

INVENTOR(S) : Raymond Baker, et al.

It is certified that error appears in the above-identified patent and that said Letters Patent is hereby corrected as shown below:

On title page, item [22]
Change filing date January 28, 1993 to January 28, 1992.

Signed and Sealed this

Sixth Day of September, 1994

*Attest:*

BRUCE LEHMAN

*Attesting Officer*      *Commissioner of Patents and Trademarks*